United States Patent [19]
Bennett et al.

[11] Patent Number: 5,883,082
[45] Date of Patent: Mar. 16, 1999

[54] COMPOSITIONS AND METHODS FOR PREVENTING AND TREATING ALLOGRAFT REJECTION

[75] Inventors: C. Frank Bennett, Carlsbad, Calif.; Stanislaw M. Stepkowski, Houston, Tex.

[73] Assignees: ISIS Pharmaceuticals, Inc.; Board of Regents, The University of Texas System, both of Austin, Tex.

[21] Appl. No.: 344,155

[22] Filed: Nov. 23, 1994

Related U.S. Application Data

[63] Continuation-in-part of Ser. No. 63,167, May 17, 1993, Pat. No. 5,514,788, which is a continuation-in-part of Ser. No. 7,997, Jan. 21, 1993, Pat. No. 5,591,623, which is a continuation-in-part of Ser. No. 939,855, Sep. 2, 1992, abandoned, which is a continuation-in-part of Ser. No. 567,286, Aug. 14, 1990, abandoned.

[51] Int. Cl.$^6$ ............................ C07H 21/04; A61K 48/00
[52] U.S. Cl. ........................... 514/44; 536/24.5; 536/23.1; 424/152.1
[58] Field of Search ................. 536/23.1, 24.5; 514/44; 424/152.1

[56] References Cited

U.S. PATENT DOCUMENTS

| | | | |
|---|---|---|---|
| 5,284,931 | 2/1994 | Springer et al. | 424/85.8 |
| 5,514,788 | 5/1996 | Bennett et al. | 536/23.1 |
| 5,580,969 | 12/1996 | Hoke et al. | 536/24.5 |
| 5,585,479 | 12/1996 | Hoke et al. | 536/24.5 |
| 5,596,090 | 1/1997 | Hoke et al. | 536/24.5 |

OTHER PUBLICATIONS

Chen et al., "Mechanism of Action of the Novel Anticancer Agent 6–Fluoro–2(2'–fluoro–1,1'–biphenyl–4–yl)–3–methyl–4–quinolinecarboxylic Acid Sodium Salt (NSC 368390): Inhibition of de Novo Pyrimidine Nucleotide Biosynthesis," *Cancer Res.* 1986, 46, 5014–5019.

Chou, T–C. et al., "Quantitative Analysis of Dose–Effect Relationships: The Combined Effects of Multiple Drugs of Enzyme Inhibitors," *Adv. Enz. Regul.* 1984, 22, 27–55.

Haug et al., "A Phase I Trial of Immunosuppression with Anti–ICAM–1 (CD54) mAb in Renal Allograft Recipients," *Transplantation* 1993, 55, 766–773.

Kitajima et al., "Ablation of Transplanted HTLV–I Tax–Transformed Tumors in Mice by Antisense Inhibition of NK–$_k$B," *Science* 1992, 258, 1792–1795.

Liu et al., "Calcineurin is a Common Target of Cyclophilin–Cyclosporin A and FKBP–FK506 Complexes," *Cell* 1991, 66, 807–815.

Monaco et al., "Studies on Heterologous Anti–Lymphocyte Serum in Mice," *J. Immunol.* 1966, 96, 229–238.

Morice et al., "Rapamycin–Induced Inhibition of p34$^{cdc2}$ Kinase Activation is Associated with G$_1$/S–Phase Growth Arrest in T Lymphocytes," *J. Biol. Chem.* 1993, 268, 3734–3738.

Nickoloff et al., "Accessory Cell Function of Keratinocytes for Superantigens," *J. Immunol.* 1993, 150, 2148–2159.

Simons et al., "Antisense c–myb Oligonucleotides Inhibit Intimal Arterial Smooth Muscle Cell Accumulation in vivo," *Nature* 1992, 359, 67–70.

Adams et al., Intercellular Adhesion Molecule 1 on Liver Allografts During Rejection, *Lancet* 1989, 1122–1125.

Bevilacqua et al., Endothelial Leukocyte Adhesion Molecule 1: An Inducible Receptor for Neutorophils Related to Complement Regulatory Proteins and Lectins, *Science* 1989, 243, 1160–1165.

Bevilacqua et al., Identification of an Inducible Endothelial–leukocyte Adhesion Molecule, *Proc. Natl. Acad. Sci. USA* 1987, 84, 9238–9242.

Cosimi et al., In vivo Effects of Monoclonal Antibody to ICAM–1 (CD54) in Nonhuman Primates with Renal Allografts, *J. Immunol.* 1990, 144, 4604–4612.

Faull et al., Tubular Expression of Interecellular Adhesion Molecule–1 During Renal Allograft Rejection, *Transplantation* 1989, 48, 226–230.

Frohman et al., The induction of intercellular adhesion molecule 1 (ICAM–1) expression on human fetal astrocytes by interferon–γ, tumor necrosis factor α, lymphotoxim, and interleukin–1: relevance to intracerebral antigen presentation, *J. Neuroimmunol.* 1989, 23, 117–124.

Harlan, J.M., Leukocyte–Endothelial Interactions, *Blood* 1985, 65, 513–525.

Isobe et al., Specific Acceptance of Cardiac Allograft After Treatment with Antibodies to ICAM–1 and LFA–1, *Science* 1992, 255, 1125–1127.

Isobe et al., Early Detection of Rejection and Assessment of Cyclosporine Therapy by $^{111}$In Antimyosin Imaging in Mouse Heart Allografts, (1991) *Circulation* 84:1246–1255.

Nielsen et al., Sequence–Selective Recognition of DNA by Strand Displacement with a Thymine–Substituted Polyamide, *Science* 1991, 254, 1497.

Osborn et al., Direct Expression Cloning of Vasular Cell Adhesion Molecule 1, a Cytokine–Induced Endothelial Protein that Binds to Lymphocytes, *Cell* 1989 59:1203–11.

Rice et al., An Inducible Endothelial Cell Surface Glycoprotein Mediates Melanoma Adhesion, *Science* 1989, 246, 1303–1306.

(List continued on next page.)

*Primary Examiner*—Lila Feisee
*Assistant Examiner*—Geetha P. Bansal
*Attorney, Agent, or Firm*—Law Offices of Jane Massey Licata

[57] ABSTRACT

Compositions and methods are provided for the prevention and treatment of allograft rejection. Compositions are provided which comprise an antisense oligonucleotide targeted to a nucleic acid sequence encoding intercellular adhesion molecule-1, vascular cell adhesion molecule-1, or endothelial leukocyte adhesion molecule-1 in combination with an immunosuppressive agent. Methods of preventing or treating allograft rejection by treating an allograft recipient with such a composition are provided. Methods for preventing allograft rejection comprising perfusion of the graft are also provided.

23 Claims, No Drawings

OTHER PUBLICATIONS

Rice et al., Inducible Cell Adhesion Molecule 110 (INCAM–110) is an Endothelial Receptor for Lymphocytes, *J. Exp. Med.* 1990, 171, 1369–1374.

Staunton et al., Primary Structure of ICAM–1 Demonstrates Interaction between Members of the Immunoglobulin and Integrin Supergene Families, *Cell* 1988, 52, 925–933.

Wellicome et al., A Monoclonal Antibody that Detects a Novel Antigen on Endothelial Cells that is Induced by Tumor Necrosis Factor, IL–1, or Lipopolysaccharide, *J. Immunol.* 1990, 144, 2558–2565.

Zuker, M., On Findings All Suboptimal Foldings of an RNA Molecule, *Science* 1989, 244, 48–52.

Chiang, M Y et al. 1991. JBC. 266(27): 18162–18171.

Kalian, B.D. et al. 1993. Transplantation 55:894–900.

Monaco, A.P. et al 1966. J. Immunol. 96(2):229–238.

COMPOSITIONS AND METHODS FOR PREVENTING AND TREATING ALLOGRAFT REJECTION

The instant application is a continuation-in-part of application Ser. No. 08/063,167 filed May 17, 1993, now issued as U.S. Pat. No. 5,514,788; which is a c-i-p of application Ser. No. 08/007,997 filed Jan. 21, 1993, now issued as U.S. Pat. No. 5,591,623; which is a c-i-p of application Ser. No. 07/939,855 filed Sep. 2, 1992, now abandoned; which is a c-i-p of application Ser. No. 07/567,286 filed Aug. 14, 1990, now abandoned.

FIELD OF THE INVENTION

This invention relates to compositions and methods for preventing and treating allograft rejection. In particular, compositions comprising an antisense oligonucleotide in combination with an immunosuppressive agent are provided. The antisense oligonucleotide is targeted to nucleic acids encoding intercellular adhesion molecule-1 (ICAM-1), endothelial leukocyte adhesion molecule-1 (ELAM-1, also known as E-selectin) or vascular cell adhesion molecule-1 (VCAM-1). The immunosuppressive agent is a monoclonal antibody, antisense oligonucleotide or conventional immunosuppressive agent such as brequinar, rapamycin or anti-lymphocyte serum. These compositions have been found to extend allograft survival times and induce donor-specific transplant tolerance. These compositions are useful for preventing and treating allograft rejection and for inducing tolerance to specific allergens or antigens.

BACKGROUND OF THE INVENTION

Inflammation is a localized protective response elicited by tissues in response to injury, infection, or tissue destruction resulting in the destruction of the infectious or injurious agent and isolation of the injured tissue. A typical inflammatory response proceeds as follows: recognition of an antigen as foreign or recognition of tissue damage; synthesis and release of soluble inflammatory mediators; recruitment of inflammatory cells to the site of infection or tissue damage; destruction and removal of the invading organism or damaged tissue; and deactivation of the system once the invading organism or damage has been resolved.

Cell-cell interactions are involved in the activation of the immune response at each of the stages described above. One of the earliest detectable events in a normal inflammatory response is adhesion of leukocytes to the vascular endothelium, followed by migration of leukocytes out of the vasculature to the site of infection or injury. The adhesion of these leukocytes, or white blood cells, to vascular endothelium is an obligate step in the migration out of the vasculature. Harlan, J. M., *Blood* 1985, 65, 513–525.

The adhesion of white blood cells to vascular endothelium and other cell types is mediated by interactions between specific proteins, termed "adhesion molecules," located on the plasma membrane of both white blood cells and vascular endothelium. The interaction between adhesion molecules is similar to classical receptor ligand interactions with the exception that the ligand is fixed to the surface of a cell instead of being soluble. The adherence of white blood cells to vascular endothelium appears to be mediated in part if not in toto by the five cell adhesion molecules: intercellular adhesion molecule-1 (ICAM-1); ICAM-2; endothelial leukocyte adhesion molecule-1 (ELAM-1, also called E-selectin); vascular cell adhesion molecule-1 (VCAM-1); and granule membrane protein-140 (GMP-140). Expression on the cell surface of ICAM-1, ICAM-2, ELAM-1, VCAM-1 and GMP-140 adhesion molecules is induced by inflammatory stimuli. The expression of ELAM-1 and VCAM-1 on endothelial cells is induced by cytokines such as interleukin-1β and tumor necrosis factor, but not gamma-interferon. ICAM-1 expression on endothelial cells is induced by the cytokines, interleukin-1 tumor necrosis factor and gamma-interferon.

In organ transplantation, the reaction of host immune cells with transplant cells is mediated by adhesive cell membrane receptors. An essential step in the activation of T lymphocytes is their interaction with endothelial cells of the graft. Binding of T lymphocytes to the endothelial cells requires intercellular adhesion molecules. It is believed that the induction of ICAM-1 influences the leukocyte response in transplanted tissue. ICAM-1 has been shown to be expressed in rejecting kidney and liver allografts; Faull and Russ, *Transplantation* 1989, 48, 226–230; Adams et al., *Lancet* 1989, 1122–1125. Other adhesion molecules, including VCAM-1 and ELAM-1, are also known to be involved in interactions between the transplanted tissue and the immune system.

It is believed that compositions comprising inhibitors of ICAM-1, VCAM-1 and ELAM-1 expression could provide a novel therapeutic class of anti-rejection agents. The use of neutralizing monoclonal antibodies against ICAM-1 in animal models provides evidence that such inhibitors, if identified, would have therapeutic benefit for renal allografts (Cosimi et al., *J. Immunol.* 1990, 144, 4604–4612) and cardiac allografts (Isobe et al., *Science* 1992, 255, 1125–1127). Experiments in monkeys have been performed to examine the effectiveness of monoclonal antibodies to ICAM-1 in blocking rejection of kidney allografts. Cosimi et al., *J. Immunol.* 1990, 144, 4604–4612. As in humans, ICAM-1 molecules are expressed on vascular endothelium in normal kidney. During rejection, ICAM-1 expression increased on endothelial and tubular cells and on leukocytes; this increase correlated with massive infiltration of grafts. Treatment with monoclonal antibody to ICAM-1 decreased cellular infiltration and allowed the necessary cyclosporine A dosage to be reduced. Clinical trials conducted in high-risk kidney allograft patients showed that treatment with mouse anti-ICAM-1 monoclonal antibody in a 14-day post-operative period in addition to the triple drug therapy (cyclosporine A, azathioprine and corticosteroids) improved one-year allograft survival from 56% to 78%. Haug et al., *Transplantation* 1993, 55, 766–773. However, the majority of patients developed human anti-mouse antibodies within the first two weeks following completion of monoclonal treatment.

Current agents which affect intercellular adhesion molecules include synthetic peptides, monoclonal antibodies, and soluble forms of the adhesion molecules. To date, synthetic peptides which block the interactions with VCAM-1 or ELAM-1 have not been identified. Monoclonal antibodies may prove to be useful for the treatment of allograft rejection due to expression of ICAM-1, VCAM-1 and ELAM-1. The role of ICAM-1 and LFA-1 molecules in graft rejection has been previously demonstrated by treatment of heart allograft recipient mice with monoclonal antibodies to ICAM-1 and LFA-1. This combined treatment induced long-term allograft survival and donor-specific transplantation tolerance. Isobe et al., *Science* 1992, 255, 1125–1127. However, with chronic treatment, the host animal develops an immune response against the monoclonal antibodies thereby limiting their usefulness in long-term therapy. Soluble forms of the cell adhesion molecules suffer from many of the same limitations as monoclonal antibodies in addition to the expense of their production and their low binding affinity. Thus, there is a long felt need for compositions which effectively inhibit allograft rejection.

PCT/US90/02357 (Hession et al.) discloses DNA sequences encoding Endothelial Adhesion Molecules (ELAMs), including ELAM-1 and VCAM-1 and VCAM-1b. A number of uses for these DNA sequences are provided, including (1) production of monoclonal antibody preparations that are reactive for these molecules which may be used as therapeutic agents to inhibit leukocyte binding to endothelial cells; (2) production of ELAM peptides to bind to the ELAM ligand on leukocytes which, in turn, may bind to ELAM on endothelial cells, inhibiting leukocyte binding to endothelial cells; (3) use of molecules binding to ELAMS (such as anti-ELAM antibodies, or markers such as the ligand or fragments of it) to detect inflammation; and (4) use of ELAM and ELAM ligand DNA sequences to produce nucleic acid molecules which intervene in ELAM or ELAM ligand expression at the translational level using antisense nucleic acid and ribozymes to block translation of a specific mRNA either by masking mRNA with antisense nucleic acid or cleaving it with a ribozyme. It is disclosed that coding regions are the targets of choice. For VCAM-1, AUG is believed to be most likely; a 15-mer hybridizing to the AUG site is specifically disclosed in Example 17 of PCT/US90/02357.

SUMMARY OF THE INVENTION

In accordance with the present invention, compositions for treating allograft rejection are provided. These compositions comprise an antisense oligonucleotide which is targeted to a nucleic acid sequence encoding ICAM-1, ELAM-1 or VCAM-1 in combination with an immunosuppressive agent.

Also in accordance with the present invention, methods of preventing or treating allograft rejection are provided which comprise treating an allograft recipient with an antisense oligonucleotide which is targeted to a nucleic acid sequence encoding ICAM-1, ELAM-1 or VCAM-1, in combination with an immunosuppressive agent.

Further in accordance with the present invention, methods of preventing rejection of an allograft are provided which comprise perfusion of the graft prior to transplantation.

DETAILED DESCRIPTION OF THE INVENTION

Recognition of an antigen as foreign is the initial step in the inflammatory response to injury, infection or tissue destruction. Allograft rejection also begins with the recognition of foreign antigens. The acute infiltration of neutrophils into the site of inflammation appears to be due to increased expression of GMP-140, ELAM-1 and ICAM-1 on the surface of endothelial cells. The appearance of lymphocytes and monocytes during the later stages of an inflammatory reaction appear to be mediated by VCAM-1 and ICAM-1. ELAM-1 and GMP-140 are transiently expressed on vascular endothelial cells, while VCAM-1 and ICAM-1 are chronically expressed.

ICAM-1 is a member of the immunoglobulin supergene family, containing 5 immunoglobulin-like domains at the amino terminus, followed by a transmembrane domain and a cytoplasmic domain. Human ICAM-1 is encoded by a 3.3-kb mRNA resulting in the synthesis of a 55,219 dalton protein. The mRNA sequence of human ICAM-1 (SEQ ID NO: 97) was described by Staunton et al., Cell 1988, 52, 925–933. The mature glycosylated protein has an apparent molecular mass of 90 kDa as determined by SDS-polyacrylamide gel electrophoresis.

ICAM-1 exhibits a broad tissue and cell distribution, and may be found on white blood cells, endothelial cells, fibroblast, keratinocytes and other epithelial cells. The expression of ICAM-1 can be regulated on vascular endothelial cells, fibroblasts, keratinocytes, astrocytes and several cell lines by treatment with bacterial lipopolysaccharide and cytokines such as interleukin-1, tumor necrosis factor, gamma-interferon, and lymphotoxin. See, e.g., Frohman et al., *J. Neuroimmunol.* 1989, 23, 117–124. Increased expression of ICAM-1 molecules correlates with increased leukocyte infiltration followed by the rejection of organ allografts in both humans and mice. Nickoloff et al., *J. Immunol.* 1993, 150, 2148–2159.

ELAM-1 is a 115-kDa membrane glycoprotein which is a member of the selectin family of membrane glycoproteins. The mRNA sequence of human ELAM-1 (SEQ ID NO:98) was described by Bevilacqua et al., *Science* 1989, 243, 1160–1165. The amino terminal region of ELAM-1 contains sequences with homologies to members of lectin-like proteins, followed by a domain similar to epidermal growth factor, followed by six tandem 60-amino acid repeats similar to those found in complement receptors 1 and 2. These features are also shared by GMP-140 and MEL-14 antigen, a lymphocyte homing antigen. ELAM-1 is encoded for by a 3.9-kb mRNA. The 3'-untranslated region of ELAM-1 mRNA contains several ATTTA sequence motifs which are responsible for the rapid turnover of cellular mRNA consistent with the transient nature of ELAM-1 expression.

ELAM-1 exhibits a limited cellular distribution in that it has only been identified on vascular endothelial cells. Like ICAM-1, ELAM-1 is inducible by a number of cytokines including tumor necrosis factor, interleukin-1 and lymphotoxin and bacterial lipopolysaccharide. In contrast to ICAM-1, ELAM-1 is not induced by gamma-interferon. Bevilacqua et al., *Proc. Natl. Acad. Sci. USA* 1987, 84, 9238–9242; Wellicome et al., *J. Immunol.* 1990, 144, 2558–2565. The kinetics of ELAM-1 mRNA induction and disappearance in human umbilical vein endothelial cells precedes the appearance and disappearance of ELAM-1 on the cell surface.

VCAM-1 is a 110-kDa membrane glycoprotein encoded by a 3.2-kb mRNA. The sequence of human VCAM-1 mRNA (SEQ ID NO: 99) was described by Osborn et al., *Cell* 1989, 59, 1203–1211. VCAM-1 appears to be encoded by a single-copy gene which can undergo alternative splicing to yield products with either six or seven immunoglobulin domains. The receptor for VCAM-1 is proposed to be CD29 (VLA-4) as demonstrated by the ability of monoclonal antibodies to CD29 to block adherence of Ramos cells to VCAM-1. VCAM-1 is expressed primarily on vascular endothelial cells. Like ICAM-1 and ELAM-1, expression of VCAM-1 on vascular endothelium is regulated by treatment with cytokines. Rice and Bevilacqua, *Science* 1989, 246, 1303–1306; Rice et al., *J. Exp. Med.* 1990, 171, 1369–1374.

The present invention employs oligonucleotides targeted to nucleic acid sequences encoding ICAM-1, VCAM-1 or ELAM-1. This relationship between an oligonucleotide and the nucleic acid sequence to which it is targeted is commonly referred to as "antisense." "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the target is a nucleic acid sequence encoding ICAM-1, VCAM-1 or ELAM-1; in other words, the gene encoding ICAM-1, VCAM-1 or ELAM-1, or mRNA expressed from the gene encoding ICAM-1, VCAM-1 or ELAM-1. The targeting process also includes determination of a site or sites within the nucleic acid sequence for the oligonucleotide interaction to occur such that the desired effect, i.e., modulation of gene expression, will result. Once the target site or sites have been identified, oligonucleotides are chosen which are sufficiently complementary to the target, i.e., hybridize sufficiently well and with sufficient specificity, to give the desired modulation.

In the context of this invention "modulation" means either inhibition or stimulation. Inhibition of target gene expression is presently the preferred form of modulation. This modulation can be measured in ways which are routine in the art, for example by Northern blot assay of mRNA expression or Western blot assay of protein expression as taught in the examples of the instant application. Effects on allograft survival and graft rejection can also be measured, as taught in the examples of the instant application. "Hybridization," in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

In preferred embodiments of this invention, oligonucleotides are provided which are targeted to mRNA encoding ICAM-1, VCAM-1 or ELAM-1. In accordance with this invention, persons of ordinary skill in the art will understand that mRNA includes not only the coding region which carries the information to encode a protein using the three letter genetic code, but also associated ribonucleotides which form a region known to such persons as the 5'-untranslated region, the 3'-untranslated region, the 5' cap region, intron regions and intron/exon or splice junction ribonucleotides. Thus, oligonucleotides may be formulated in accordance with this invention which are targeted wholly or in part to these associated ribonucleotides as well as to the coding ribonucleotides. The functions of messenger RNA to be interfered with include all vital functions such as translocation of the RNA to the site for protein translation, actual translation of protein from the RNA, splicing or maturation of the RNA and possibly even independent catalytic activity which may be engaged in by the RNA. The overall effect of such interference with the RNA function is to cause interference with ICAM-1, VCAM-1 or ELAM-1 protein expression.

In the context of this invention, the term "oligonucleotide" refers to an oligomer or polymer of nucleotide or nucleoside monomers consisting of naturally occurring bases, sugars and intersugar (backbone) linkages. The term "oligonucleotide" also includes oligomers or polymers comprising non-naturally occurring monomers, or portions thereof, which function similarly. Such modified or substituted oligonucleotides are often preferred over native forms because of properties such as, for example, enhanced cellular uptake, increased stability in the presence of nucleases, or enhanced target affinity. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A number of modifications have also been shown to increase binding (affinity) of the oligonucleotide to its target. Affinity of an oligonucleotide for its target (in this case, a nucleic acid sequence encoding ICAM-1, ELAM-1 or VCAM-1) is routinely determined by measuring the Tm of an oligonucleotide/target pair, which is the temperature at which the oligonucleotide and target dissociate. Dissociation is detected spectrophotometrically. The higher the Tm, the greater the affinity of the oligonucleotide for the target. In some cases, oligonucleotide modifications which enhance target binding affinity are also, independently, able to enhance nuclease resistance.

Specific examples of some preferred oligonucleotides envisioned for this invention may contain phosphorothioates, phosphotriesters, methyl phosphonates, short chain alkyl or cycloalkyl intersugar linkages or short chain heteroatomic or heterocyclic intersugar ("backbone") linkages. Most preferred are phosphorothioates and those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$). Also preferred are oligonucleotides having morpholino backbone structures. Summerton, J. E. and Weller, D. D., U.S. Pat. No: 5,034,506. In other preferred embodiments, such as the protein-nucleic acid or peptide-nucleic acid (PNA) backbone, the phosphodiester backbone of the oligonucleotide may be replaced with a polyamide backbone, the bases being bound directly or indirectly to the aza nitrogen atoms of the polyamide backbone. P. E. Nielsen, M. Egholm, R. H. Berg, O. Buchardt, *Science* 1991, 254, 1497. Other preferred oligonucleotides may contain alkyl and halogen-substituted sugar moieties comprising one of the following at the 2' position: OH, SH, $SCH_3$, F, OCN, $OCH_3OCH_3$, $OCH_3O(CH_2)_nCH_3$, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a cholesteryl group; a reporter group; an intercalator; a group for improving the pharmacokinetic properties of an oligonucleotide; or a group for improving the pharmacodynamic properties of an oligonucleotide and other substituents having similar properties. Oligonucleotides may also have sugar mimetics such as cyclobutyls in place of the pentofuranosyl group. Other preferred embodiments may include at least one modified base form or "universal base" such as inosine.

The oligonucleotides in accordance with this invention preferably are from about 8 to about 50 nucleotides in length. In the context of this invention it is understood that this encompasses non-naturally occurring oligomers as hereinbefore described, having 8 to 50 monomers.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is also well known to use similar techniques to prepare other oligonucleotides such as the phosphorothioates and alkylated derivatives. It is also well known to use similar techniques and commercially available modified amidites and controlled-pore glass (CPG) products such as those available from Glen Research, Sterling Va., to synthesize modified oligonucleotides such as cholesterol-modified oligonucleotides.

For prophylactics and therapeutics, methods of preventing and treating allograft rejection are provided. The formulation of therapeutic compositions and their subsequent administration is believed to be within the skill in the art. In accordance with some embodiments of this invention, an allograft recipient is treated by administering compositions comprising an antisense oligonucleotide targeted to ICAM-1, VCAM-1 or ELAM-1 in combination with an immunosuppressive agent. In the context of the present invention, "in combination" means that the oligonucleotide and immunosuppressive agent are administered in the same course of treatment and may be administered separately, simultaneously or in a mixture, i.e., a single composition or formulation containing both oligonucleotide and immunosuppressive agent. Examples of immunosuppressive agents include conventional immunosuppressive agents, of which brequinar, rapamycin, and anti-lymphocyte serum are preferred, and monoclonal antibodies, of which those directed to LFA-1 are preferred. The immunosuppressive agent may also be an antisense oligonucleotide. Preferred among these are oligonucleotides targeted to B7-2 or LFA-1, or oligonucleotides targeted to ICAM-1, VCAM-1 or ELAM-1.

Oligonucleotides and/or immunosuppressive agents, or combinations of the two, may be formulated in a pharmaceutical composition, which may include carriers, thickeners, diluents, buffers, preservatives, surface active agents, liposomes or lipid formulations and the like in addition to the oligonucleotide. Pharmaceutical compositions may also include one or more active ingredients such as antimicrobial agents, anti-inflammatory agents, anesthetics, and the like. Formulations for parenteral administration may include sterile aqueous solutions which may also contain buffers, liposomes, diluents and other suitable additives.

The pharmaceutical composition may be administered in a number of ways depending on whether local or systemic treatment is desired, and on the area to be treated. Administration may be topical (including ophthalmic, vaginal, rectal, intranasal), oral, by inhalation, or parenteral, for example by intravenous drip, subcutaneous, intraperitoneal or intramuscular injection. In the present invention, intraperitoneal injection, oral gavage or intravenous infusion by osmotic pump are preferred modes of administration.

Dosing is dependent on severity and responsiveness of the condition to be treated, with course of treatment lasting from several days to several months or until a cure is effected or a diminution of disease state is achieved. Optimal dosing schedules can be calculated from measurements of drug accumulation in the body. Persons of ordinary skill can easily determine optimum dosages, dosing methodologies and repetition rates. Optimum dosages may vary depending on the relative potency of individual compositions, and can generally be estimated based on EC50's in in vitro and animal studies. In general, dosage is from 0.001 μg to 100 g and may be administered once or several times daily, weekly, monthly or yearly, or even every 2 to 20 years.

For prevention of allograft rejection, ex vivo perfusion of the allograft prior to transplantation may be preferred. Methods of organ perfusion are well known in the art. In general, harvested tissues or organs (preferably heart or kidney) are perfused with the compositions of the invention in a pharmacologically acceptable carrier such as, for example, lactated Ringer's solution, University of Wisconsin (UW) solution, Euro-Collins solution or Sachs solution. Simple flushing of the organ or pulsatile perfusion may be used. Perfusion time is generally dependent on the length of ex vivo viability of the organ being transplanted; these viability times vary from organ to organ and are known in the art. Hearts and livers, for example, are generally transplanted within 4 to 6 hours of harvesting, whereas other organs may have longer ischemic viability. Kidneys, for example, may be transplanted up to 48 hr or even 72 hr after harvesting. Dosage may range from 0.001 μg to 500 g each of oligonucleotide and immunosuppressive agent.

Several preferred embodiments of this invention are exemplified in accordance with the following nonlimiting examples. Persons of ordinary skill in the art will appreciate that the present invention is not so limited, however, and that it is generally applicable.

EXAMPLES

Example 1

Synthesis and characterization of oligonucleotides

Unmodified DNA oligonucleotides were synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For phosphorothioate oligonucleotides, the standard oxidation bottle was replaced by a 0.2M solution of 3H-1,2-benzodithiole-3-one 1,1-dioxide in acetonitrile for the stepwise thiation of the phosphite linkages. The thiation cycle wait step was increased to 68 seconds and was followed by the capping step.

After cleavage from the controlled pore glass column (Applied Biosystems) and deblocking in concentrated ammonium hydroxide at 55° C. for 18 hours, the oligonucleotides were purified by precipitation twice out of 0.5M NaCl with 2.5 volumes ethanol. Analytical gel electrophoresis was accomplished in 20% acrylamide, 8M urea, 45 mM Tris-borate buffer, pH 7.0. Oligodeoxynucleotides and phosphorothioate oligonucleotides were judged from electrophoresis to be greater than 80% full length material.

The relative amounts of phosphorothioate and phosphodiester linkages obtained by this synthesis were periodically checked by $^{31}$P NMR spectroscopy. The spectra were obtained at ambient temperature using deuterium oxide or dimethyl sulfoxide-$d_6$ as solvent. Phosphorothioate samples typically contained less than one percent of phosphodiester linkages.

Secondary evaluation was performed with oligonucleotides purified by trityl-on HPLC on a PRP-1 column (Hamilton Co., Reno, Nev.) using a gradient of acetonitrile in 50 mM triethylammonium acetate, pH 7.0 (4% to 32% in 30 minutes, flow rate=1.5 ml/min). Appropriate fractions were pooled, evaporated and treated with 5% acetic acid at ambient temperature for 15 minutes. The solution was extracted with an equal volume of ethyl acetate, neutralized with ammonium hydroxide, frozen and lyophilized. HPLC-purified oligonucleotides were not significantly different in potency from precipitated oligonucleotides, as judged by the ELISA assay for ICAM-1 expression.

Example 2
Quantitation of ICAM-1, VCAM-1 and ELAM-1 expression by ELISA

Expression of ICAM-1, VCAM-1 and ELAM-1 on the surface of cells was quantitated using specific monoclonal antibodies in an ELISA. Cells were grown to confluence in 96-well microtiter plates. The cells were stimulated with either interleukin-1 or tumor necrosis factor for 4 to 8 hours to quantitate ELAM-1 and 8 to 24 hours to quantitate ICAM-1 and VCAM-1. Following the appropriate incubation time with the cytokine, the cells were gently washed three times with a buffered isotonic solution containing calcium and magnesium such as Dulbecco's phosphate buffered saline (D-PBS). The cells were then directly fixed on the microtiter plate with 1 to 2% paraformaldehyde diluted in D-PBS for 20 minutes at 25° C. The cells were washed again with D-PBS three times. Nonspecific binding sites on the microtiter plate were blocked with 2% bovine serum albumin in D-PBS for 1 hour at 37° C. Cells were incubated with the appropriate monoclonal antibody diluted in blocking solution for 1 hour at 37° C. Unbound antibody was removed by washing the cells three times with D-PBS. Antibody bound to the cells was detected by incubation with a 1:1000 dilution of biotinylated goat anti-mouse IgG (Bethesda Research Laboratories, Gaithersberg, Md.) in blocking solution for 1 hour at 37° C. Cells were washed three times with D-PBS and then incubated with a 1:1000 dilution of streptavidin conjugated to β-galactosidase (Bethesda Research Laboratories) for 1 hour at 37° C. The cells were washed three times with D-PBS for 5 minutes each. The amount of β-galactosidase bound to the specific monoclonal antibody was determined by developing the plate in a solution of 3.3 mM chlorophenolred-β-D-galactopyranoside, 50 mM sodium phosphate, 1.5 mM $MgCl_2$; pH=7.2 for 2 to 15 minutes at 37° C. The concentration of the product was determined by measuring the absorbance at 575 nm in an ELISA microtiter plate reader.

Induction of ICAM-1 was observed following stimulation with either interleukin-1β or tumor necrosis factor α in several human cell lines. Cells were stimulated with increasing concentrations of interleukin-1 or tumor necrosis factor for 15 hours and processed as described above. ICAM-1 expression was determined by incubation with a 1:1000 dilution of the monoclonal antibody 84H10 (Amac Inc., Westbrook, Me.). The cell lines used were passage 4 human umbilical vein endothelial cells (HUVEC), a human epidermal carcinoma cell line (A431), a human melanoma cell line (SK-MEL-2) and a human lung carcinoma cell line (A549). ICAM-1 was induced on all the cell lines; however, tumor necrosis factor was more effective than interleukin-1 in induction of ICAM-1 expression on the cell surface.

Screening antisense oligonucleotides for inhibition of ICAM-1, VCAM-1 or ELAM-1 expression was performed as described above with the exception of pretreatment of cells with the oligonucleotides prior to challenge with the cytokines. Human umbilical vein endothelial cells (HUVEC) were treated with increasing concentration of oligonucleotide diluted in Opti MEM (GIBCO, Grand Island, N.Y.) containing 8 μM N-[1-(2,3-dioleyloxy) propyl] -N,N,N-trimethylammonium chloride (DOTMA) for 4 hours at 37° C. to enhance uptake of the oligonucleotides. The medium was removed and replaced with endothelial growth medium (EGM-UV; Clonetics, San Diego, Calif.) containing the indicated concentration of oligonucleotide for an additional 4 hours. Interleukin-1β was added to the cells at a concentration of 5 units/ml and incubated for 14 hours at 37° C. The cells were quantitated for ICAM-1 expression using a 1:1000 dilution of the monoclonal antibody 84H10 as described above. The oligonucleotides used were:

COMPOUND 1—(ISIS 1558) a phosphodiester oligonucleotide targeted to position 64–80 of the mRNA covering the AUG initiation of translation codon having the sequence 5'-TGGGAGCCATAGCGAGGC-3' (SEQ ID NO: 1).

COMPOUND 2—(ISIS 1570) a phosphorothioate oligonucleotide corresponding to the same sequence as COMPOUND 1.

COMPOUND 3—a phosphorothioate oligonucleotide complementary to COMPOUND 1 and COMPOUND 2 exhibiting the sequence
5'-GCCTCGCTATGGCTCCCA-3' (SEQ ID NO: 81).

COMPOUND 4—(ISIS 1572) a phosphorothioate oligonucleotide targeted to positions 2190–2210 of the mRNA in the 3' untranslated region containing the sequence
5'-GACACTCAATAAATAGCTGGT-3' (SEQ ID NO: 3).

COMPOUND 5—(ISIS 1821) a phosphorothioate oligonucleotide targeted to human 5-lipoxygenase mRNA used as a control containing the sequence
5'-CATGGCGCGGGCCGCGGG-3' (SEQ ID NO: 82).

The phosphodiester oligonucleotide targeting the AUG initiation of translation region of the human ICAM-1 mRNA (COMPOUND 1) did not inhibit expression of ICAM-1; however, the corresponding phosphorothioate oligonucleotide (COMPOUND 2) inhibited ICAM-1 expression by 70% at a concentration of 0.1 μM and 90% at 1 μM concentration. The increased potency of the phosphorothioate oligonucleotide over the phosphodiester is due to increased stability. The sense strand to COMPOUND 2, COMPOUND 3, inhibited ICAM-1 expression by 25% at 10 μM. If COMPOUND 2 was prehybridized to COMPOUND 3 prior to addition to the cells, the effects of COMPOUND 2 on ICAM-1 expression were attenuated suggesting that the activity of COMPOUND 2 was due to antisense oligonucleotide effect, requiring hybridization to the mRNA. The antisense oligonucleotide directed against 3' untranslated sequences (COMPOUND 4) inhibited ICAM-1 expression by 62% at a concentration of 1 μM. The control oligonucleotide, targeting human 5-lipoxygenase (COMPOUND 5), reduced ICAM-1 expression by 20%. These data demonstrate that oligonucleotides are capable of inhibiting ICAM-1 expression on human umbilical vein endothelial cells and suggest that the inhibition of ICAM-1 expression is due to an antisense activity.

The antisense oligonucleotide COMPOUND 2 at a concentration of 1 μM was shown to inhibit expression of ICAM-1 on human umbilical vein endothelial cells stimulated with either tumor necrosis factor or interleukin-1.

These data demonstrate that the effects of COMPOUND 2 are not specific for stimulation of cells by a particular cytokine.

Example 3
Cell adherence assay

A second cellular assay which was used to demonstrate the effects of antisense oligonucleotides on ICAM-1, VCAM-1 or ELAM-1 expression was a cell adherence assay. Target cells were grown as a monolayer in a multiwell plate, treated with oligonucleotide followed by cytokine. The adhering cells were then added to the monolayer cells and incubated for 30 to 60 minutes at 37° C. and washed to remove nonadhering cells. Cells adhering to the monolayer may be determined either by directly counting the adhering cells or prelabeling the cells with a radioisotope such as $^{51}$Cr and quantitating the radioactivity associated with the monolayer as described. Dustin and Springer, *J. Cell Biol.* 1988, 107, 321–331.

An example of the effects of antisense oligonucleotides targeting ICAM-1 mRNA on the adherence of DMSO differentiated HL-60 cells to tumor necrosis factor treated human umbilical vein endothelial cells is as follows. Human umbilical vein endothelial cells were grown to 80% confluence in 12 well plates. The cells were treated with 2 µM oligonucleotide diluted in Opti-MEM containing 8 µM DOTMA for 4 hours at 37° C. The medium was removed and replaced with fresh endothelial cell growth medium (EGM-UV) containing 2 µM of the indicated oligonucleotide and incubated 4 hours at 37° C. Tumor necrosis factor, 1 ng/ml, was added to cells as indicated and cells incubated for an additional 19 hours. The cells were washed once with EGM-UV and 1.6×10$^6$ HL-60 cells differentiated for 4 days with 1.3% DMSO added. The cells were allowed to attach for 1 hour at 37° C. and gently washed 4 times with Dulbecco's phosphate-buffered saline (D-PBS) warmed to 37° C. Adherent cells were detached from the monolayer by addition of 0.25 ml of cold (4° C.) phosphate-buffered saline containing 5 mM EDTA and incubated on ice for 5 minutes. The number of cells removed by treatment with EDTA was determined by counting with a hemocytometer. Endothelial cells detached from the monolayer by EDTA treatment could easily be distinguished from HL-60 cells by morphological differences.

In the absence of tumor necrosis factor, 3% of the HL-60 cells bound to the endothelial cells. Treatment of the endothelial cell monolayer with 1 ng/ml tumor necrosis factor increased the number of adhering cells to 59% of total cells added. Treatment with the antisense oligonucleotide COMPOUND 2 or the control oligonucleotide COMPOUND 5 did not change the number of cells adhering to the monolayer in the absence of tumor necrosis factor treatment. The antisense oligonucleotide, COMPOUND 2, reduced the number of adhering cells from 59% of total cells added to 17% of the total cells added. In contrast, the control oligonucleotide, COMPOUND 5, did not significantly reduce the number of cells adhering to the tumor necrosis factor treated endothelial monolayer, i.e., 53% of total cells added for COMPOUND 5 treated cells versus 59% for control cells.

These data indicate that antisense oligonucleotides are capable of inhibiting ICAM-1 expression on endothelial cells and that inhibition of ICAM-1 expression correlates with a decrease in the adherence of a neutrophil-like cell to the endothelial monolayer in a sequence specific fashion. Because other molecules, such as ELAM-1 and VCAM-1, also mediate adherence of white blood cells to endothelial cells, it is not expected that adherence would be completely blocked by antisense to ICAM-1.

Example 4
Cell culture and treatment with oligonucleotides

The human lung carcinoma cell line A549 was obtained from the American Type Culture Collection (Bethesda Md.). Cells were grown in Dulbecco's Modified Eagle's Medium (Irvine Scientific, Irvine Calif.) containing 1 gm glucose/liter and 10% fetal calf serum (Irvine Scientific). Human umbilical vein endothelial cells (HUVEC) (Clonetics, San Diego Calif.) were cultured in EGM-UV medium (Clonetics). HUVEC were used between the second and sixth passages. Human epidermal carcinoma A431 cells were obtained from the American Type Culture Collection and cultured in DMEM with 4.5 g/l glucose. Primary human keratinocytes were obtained from Clonetics and grown in KGM (Keratinocyte growth medium, Clonetics).

Cells grown in 96-well plates were washed three times with Opti-MEM (GIBCO, Grand Island, N.Y.) prewarmed to 37° C. 100 µl of Opti-MEM containing either 10 µg/ml N-[1-(2,3-dioleyloxy)propyl]-N,N,N-trimethylammonium chloride (DOTMA, Bethesda Research Labs, Bethesda Md.) in the case of HUVEC cells or 20 µg/ml DOTMA in the case of A549 cells was added to each well. Oligonucleotides were sterilized by centrifugation through 0.2 µm Centrex cellulose acetate filters (Schleicher and Schuell, Keene, N.H.). Oligonucleotides were added as 20× stock solution to the wells and incubated for 4 hours at 37° C. Medium was removed and replaced with 150 µl of the appropriate growth medium containing the indicated concentration of oligonucleotide. Cells were incubated for an additional 3 to 4 hours at 37° C. then stimulated with the appropriate cytokine for 14 to 16 hours, as indicated. ICAM-1 expression was determined as described in Example 2. The presence of DOTMA during the first 4 hours incubation with oligonucleotide increased the potency of the oligonucleotides at least 100-fold. This increase in potency correlated with an increase in cell uptake of the oligonucleotide.

Example 5
ELISA screening of additional antisense oligonucleotides for activity against ICAM-1 gene expression in Interleukin-1β-stimulated cells Antisense oligonucleotides were originally targeted to five sites on the human ICAM-1 mRNA. Oligonucleotides were synthesized in both phosphodiester (P=O; ISIS 1558, 1559, 1563, 1564 and 1565) and phosphorothioate (P=S; ISIS 1570, 1571, 1572, 1573, and 1574) forms. The oligonucleotides are shown in Table 1.

TABLE 1

ANTISENSE OLIGONUCLEOTIDES WHICH TARGET HUMAN ICAM-1

| ISIS NO. | SEQ ID NO. | TARGET REGION | MODIFICATION |
|---|---|---|---|
| 1558 | 1 | AUG Codon (64–81) | P=O |
| 1559 | 2 | 5'-Untranslated (32–49) | P=O |
| 1563 | 3 | 3'-Untranslated (2190–3010) | P=O |
| 1564 | 4 | 3'-Untranslated (2849–2866) | P=O |
| 1565 | 5 | Coding Region (1378–1395) | P=O |
| 1570 | 1 | AUG Codon (64–81) | P=S |
| 1571 | 2 | 5'-Untranslated (32–49) | P=S |
| 1572 | 3 | 3'-Untranslated (2190–3010) | P=S |
| 1573 | 4 | 3'-Untranslated (2849–2866) | P=S |
| 1574 | 5 | Coding Region (1378–1395) | P=S |
| 1930 | 6 | 5'-Untranslated (1–20) | P=S |
| 1931 | 7 | AUG Codon (55–74) | P=S |
| 1932 | 8 | AUG Codon (72–91) | P=S |
| 1933 | 9 | Coding Region (111–130) | P=S |

TABLE 1-continued

ANTISENSE OLIGONUCLEOTIDES WHICH TARGET HUMAN ICAM-1

| ISIS NO. | SEQ ID NO. | TARGET REGION | MODIFICATION |
|---|---|---|---|
| 1934 | 10 | Coding Region (351–370) | P=S |
| 1935 | 11 | Coding Region (889–908) | P=S |
| 1936 | 12 | Coding Region (1459–1468) | P=S |
| 1937 | 13 | Termination Codon (1651–1687) | P=S |
| 1938 | 14 | Termination Codon (1668–1687) | P=S |
| 1939 | 15 | 3'-Untranslated (1952–1971) | P=S |
| 1940 | 16 | 3'-Untranslated (2975–2994) | P=S |
| 2149 | 17 | AUG Codon (64–77) | P=s |
| 2163 | 18 | AUG Codon (64–75) | P=S |
| 2164 | 19 | AUG Codon (64–73) | P=S |
| 2165 | 20 | AUG Codon (66–80) | P=S |
| 2173 | 21 | AUG Codon (64–79) | P=S |
| 2302 | 22 | 3'-Untranslated (2114–2133) | P=S |
| 2303 | 23 | 3'-Untranslated (2039–2058) | P=S |
| 2304 | 24 | 3'-Untranslated (1895–1914) | P=S |
| 2305 | 25 | 3'-Untranslated (1935–1954) | P=s |
| 2307 | 26 | 3'-Untranslated (1976–1995) | P=S |
| 2634 | 1 | AUG-Codon (64–81) | 2'-fluoro A, C & U; P=S |
| 2637 | 15 | 3'-Untranslated (1952–1971) | 2'-fluoro A, C & U; P=O, except last 3 bases, P=S |
| 2691 | 1 | AUG Codon (64–81) | |
| 2710 | 15 | 3'-Untranslated (1952–1971) | 2'-O-methyl; P=O |
| 2711 | 1 | AUG Codon (64–81) | 2'-O-methyl; P=O |
| 2973 | 15 | 3'-Untranslated (1952–1971) | 2'-O-methyl; P=S |
| 2974 | 1 | AUG Codon (64–81) | 2'-O-methyl; P=S |
| 3064 | 27 | 5'-CAP (32–51) | P=S; G & C added as spacer to 3' |
| 3067 | 84 | 5'-CAP (32–51) | P=S |
| 3222 | 84 | 5'-CAP (32–51) | 2'-O-methyl; P=O |
| 3224 | 84 | 5'-CAP (32–51) | 2'-O-methyl; P=S |
| 3581 | 85 | 3'-Untranslated (1959–1978) | P=S |

Based on the initial data obtained with the five original targets, additional oligonucleotides targeted to the ICAM-1 mRNA were tested. The antisense oligonucleotide (ISIS 3067) which is targeted to the predicted transcription initiation site (5' cap site) inhibited ICAM-1 expression by nearly 90% in IL-1β-stimulated cells. ISIS 1931 and 1932 are targeted 5' and 3', respectively, to the AUG translation initiation codon. All three oligonucleotides targeted to the AUG region inhibit ICAM-1 expression, though ISIS 1932 yielded approximately 20% inhibition and thus was less active than ISIS 1570 (70% inhibition) or ISIS 1931 (>50% inhibition). Oligonucleotides targeted to the coding region of ICAM-1 mRNA (ISIS 1933, 1934, 1935, 1574 and 1936) exhibited weak activity. Oligonucleotides targeted to the translation termination codon (ISIS 1937 and 1938) exhibited moderate activity, e.g., over 50% inhibition in the case of ISIS 1938.

Surprisingly, the most active antisense oligonucleotide was ISIS 1939, a phosphorothioate oligonucleotide targeted to a sequence in the 3'-untranslated region of ICAM-1 mRNA (see Table 1). This oligonucleotide gave complete inhibition of ICAM-1 expression. Oligonucleotides targeted to other 3' untranslated sequences (ISIS 1572, 1573 and 1940) were not as active as ISIS 1939.

Because ISIS 1939 unexpectedly exhibited the greatest antisense activity of the original 16 oligonucleotides tested, other oligonucleotides targeted to sequences in the 3'-untranslated region of ICAM-1 mRNA (ISIS 2302, 2303, 2304, 2305, and 2307, as shown in Table 1) were tested. ISIS 2307, which is targeted to a site only five bases 3' to the ISIS 1939 target, was the least active of the series, and still showed nearly 70% inhibition of ICAM expression. ISIS 2302, which is targeted to the ICAM-1 mRNA at a position 143 bases 3' to the ISIS 1939 target, was the most active of the series, with nearly 100% inhibition. Examination of the predicted RNA secondary structure of the human ICAM-1 mRNA 3'-untranslated region (according to M. Zuker, *Science* 1989, 244, 48–52) revealed that both ISIS 1939 and ISIS 2302 are targeted to sequences predicted to be in a stable stem-loop structure. However, it is generally believed that regions of RNA secondary structure should be avoided when designing antisense oligonucleotides. Thus, ISIS 1939 and ISIS 2302 would not have been predicted to inhibit ICAM-1 expression.

The control oligonucleotide ISIS 1821 showed a small amount of activity against ICAM expression, probably due in part to its ability to hybridize (12 of 13 base match) to the ICAM-1 mRNA at a position 15 bases 3' to the AUG translation initiation codon.

These studies indicate that the AUG translation initiation codon and specific 3'-untranslated sequences in the ICAM-1 mRNA were the most susceptible to antisense oligonucleotide inhibition of ICAM-1 expression.

In addition to inhibiting ICAM-1 expression in human umbilical vein cells and the human lung carcinoma cells (A549), ISIS 1570, ISIS 1939 and ISIS 2302 were shown to inhibit ICAM-1 expression in primary human keratinocytes by nearly 70%, over 80% and over 80%, respectively. These oligonucleotides also inhibited ICAM-1 expression in the human epidermal carcinoma A431 cells. These data demonstrate that antisense oligonucleotides are capable of inhibiting ICAM-1 expression in several human cell lines. Furthermore, the rank order potency of the oligonucleotides is the same in the four cell lines examined.

Example 6

Specificity of antisense inhibition of ICAM-1

The specificity of the antisense oligonucleotides ISIS 1570 and ISIS 1939 for ICAM-1 was evaluated by immunoprecipitation of $^{35}$S-labelled proteins. A549 cells were grown to confluence in 25 cm$^2$ tissue culture flasks and treated with antisense oligonucleotides as described in Example 4. The cells were stimulated with interleukin-1β for 14 hours, washed with methionine-free DMEM plus 10% dialyzed fetal calf serum, and incubated for 1 hour in methionine-free medium containing 10% dialyzed fetal calf serum, 1 μM oligonucleotide and interleukin-1β as indicated. $^{35}$S-Methionine/cysteine mixture (Tran$^{35}$S-label, purchased from ICN, Costa Mesa, Calif.) was added to the cells to an activity of 100 μCi/ml and the cells were incubated an additional 2 hours. Cellular proteins were extracted by incubation with 50 mM Tris-HCl pH 8.0, 150 mM NaCl, 1.0% NP-40, 0.5% deoxycholate and 2 mM EDTA (0.5 ml per well) at 4° C. for 30 minutes. The extracts were clarified by centrifugation at 18,000× g for 20 minutes. The supernatants were preadsorbed with 200 μl protein G-Sepharose beads (Bethesda Research Labs, Bethesda Md.) for 2 hours at 4° C., divided equally and incubated with either 5 μg ICAM-1 monoclonal antibody (purchased from AMAC Inc., Westbrook Me.) or HLA-A,B antibody (W6/32, produced by murine hybridoma cells obtained from the American Type Culture Collection, Bethesda, Md.) for 15 hours at 4° C. Immune complexes were trapped by incubation with 200 μl of a 50% suspension of protein G-Sepharose (v/v) for 2 hours at 4° C., washed 5 times with lysis buffer and resolved on an SDS-polyacrylamide gel. Proteins were detected by autoradiography.

Treatment of A549 cells with 5 units/ml of interleukin-1β was shown to result in the synthesis of a 95–100 kDa protein migrating as a doublet which was immunoprecipitated with the monoclonal antibody to ICAM-1. The appearance as a doublet is believed to be due to differently glycosylated forms of ICAM-1. Pretreatment of the cells with the antisense oligonucleotide ISIS 1570 at a concentration of 1 μM decreased the synthesis of ICAM-1 by approximately 50%, while 1 μM ISIS 1939 decreased ICAM-1 synthesis to near background. Antisense oligonucleotide ISIS 1940, inactive in the ICAM-1 ELISA assay (Examples 2 and 5) did not significantly reduce ICAM-1 synthesis. None of the antisense oligonucleotides targeted to the ICAM-1 gene had a demonstrable effect on HLA-A, B synthesis, demonstrating the specificity of the oligonucleotides for ICAM-1. Furthermore, the proteins which nonspecifically precipitated with the ICAM-1 antibody and protein G-Sepharose were not significantly affected by treatment with the antisense oligonucleotides.

Example 7

Screening of additional antisense oligonucleotides for activity against ICAM-1 by cell adhesion assay Human umbilical vein endothelial (HUVEC) cells were grown and treated with oligonucleotides as in Example 4. Cells were treated with either ISIS 1939, ISIS 1940, or the control oligonucleotide ISIS 1821 for 4 hours, then stimulated with TNF-α for 20 hours. Basal HUVEC minimally bound HL-60 cells, while TNF-stimulated HUVEC bound 19% of the total cells added. Pretreatment of the HUVEC monolayer with 0.3 μM ISIS 1939 reduced the adherence of HL-60 cells to basal levels. The control oligonucleotide, ISIS 1821, and ISIS 1940 reduced the percentage of cells adhering from 19% to 9%. These data indicate that antisense oligonucleotides targeting ICAM-1 can specifically decrease adherence of a leukocyte-like cell line (HL-60) to TNF-α-treated HUVEC.

Example 8

ELISA screening of antisense oligonucleotides for activity against ELAM-1 gene expression Primary human umbilical vein endothelial (HUVEC) cells, passage 2 to 5, were plated in 96-well plates and allowed to reach confluence. Cells were washed three times with Opti-MEM (GIBCO, Grand Island N.Y.). Cells were treated with increasing concentrations of oligonucleotide diluted in Opti-MEM containing 10 μg/ml DOTMA solution (Bethesda Research Labs, Bethesda Md.) for 4 hours at 37° C. The medium was removed and replaced with EGM-UV (Clonetics, San Diego Calif.) plus oligonucleotide. Tumor necrosis factor α was added to the medium (2.5 ng/ml) and the cells were incubated an additional 4 hours at 37° C.

ELAM-1 expression was determined by ELISA. Cells were gently washed three times with Dulbecco's phosphate-buffered saline (D-PBS) prewarmed to 37° C. Cells were fixed with 95% ethanol at 4° C. for 20 minutes, washed three times with D-PBS and blocked with 2% BSA in D-PBS. Cells were incubated with ELAM-1 monoclonal antibody BBA-1 (R&D Systems, Minneapolis Minn.) diluted to 0.5 μg/ml in D-PBS containing 2% BSA for 1 hour at 20 37° C. Cells were washed three times with D-PBS and the bound ELAM-1 antibody detected with biotinylated goat anti-mouse secondary antibody followed by β-galactosidase-conjugated streptavidin as described in Example 2.

The activity of antisense phosphorothioate oligonucleotides which target 11 different regions on the ELAM-1 cDNA and two oligonucleotides which target ICAM-1 (as controls) was determined using the ELAM-1 ELISA. The oligonucleotide and targets are shown in Table 2.

TABLE 2

ANTISENSE OLIGONUCLEOTIDES WHICH TARGET HUMAN ELAM-1

| ISIS NO. | SEQ ID NO. | TARGET REGION | MODIFICATION |
|---|---|---|---|
| 1926 | 28 | AUG Codon (143–164) | P=S |
| 2670 | 29 | 3'-Untranslated (3718–3737) | P=S |
| 2673 | 30 | 3'-Untranslated (2657–2677) | P=S |
| 2674 | 31 | 3'-Untranslated (2617–2637) | P=S |
| 2678 | 32 | 3'-Untranslated (3558–3577) | P=S |
| 2679 | 33 | 5'-Untranslated (41–60) | P=S |
| 2680 | 34 | 3'-Untranslated (3715–3729) | P=S |
| 2683 | 35 | AUG Codon (143–163) | P=S |
| 2686 | 36 | AUG Codon (149–169) | P=s |
| 2687 | 37 | 5'-Untranslated (18–37) | P=S |
| 2693 | 38 | 3'-Untranslated (2760–2788) | P=S |
| 2694 | 39 | 3'-Untranslated (2934–2954) | P=S |

In contrast to what was observed with antisense oligonucleotides targeted to ICAM-1 (Example 5), the most potent oligonucleotide modulator of ELAM-1 activity (ISIS 2679) was targeted to a specific sequence in the 5'-untranslated region of ELAM-1. This oligonucleotide completely inhibited ELAM-1 expression. ISIS 2687, an oligonucleotide which targeted to sequences ending three bases upstream of the ISIS 2679 target, showed only 10–15% inhibition. Therefore, ISIS 2679 is targeted to a site on the ELAM-1 mRNA, which is sensitive to inhibition with antisense oligonucleotides. The sensitivity of this site to inhibition with antisense oligonucleotides was not predictable based upon RNA secondary structure predictions or information in the literature.

Example 9

ELISA screening of additional antisense oligonucleotides for activity against ELAM-1 gene expression Inhibition of ELAM-1 expression by eighteen antisense phosphorothioate oligonucleotides was determined using the ELISA assay as described in Example 8. The sequence and activity of each oligonucleotide against ELAM-1 are shown in Table 3. The oligonucleotides indicated by an asterisk (*) IC50's of approximately 50 nM or below and are preferred. IC50 indicates the dosage of oligonucleotide which results in 50% inhibition of ELAM-1 expression. An additional oligonucleotide targeted to the 3'-untranslated region (ISIS 4723) did not inhibit ELAM expression.

TABLE 3

Inhibition of human ELAM-1 expression by antisense oligonucleotides
ELAM-1 expression is given as % of control

| | | | | | VCAM-1 EXPRESSION | |
|---|---|---|---|---|---|---|
| ISIS # | SEQ ID # | POSITION | | SEQUENCE | 30 nM oligo | 50 nM oligo |
| *4764 | 52 | 5'-UTR | 1–19 | GAAGTCAGCCAAGAACAGCT | 70.2 | 50.2 |
| 2687 | 37 | 5'-UTR | 17–36 | TATAGGAGTTTTGATGTGAA | 91.1 | 73.8 |
| *2679 | 33 | 5'-UTR | 40–59 | CTGCTGCCTCTGTCTCAGGT | 6.4 | 6.0 |
| *4759 | 53 | 5'-UTR | 64–83 | ACAGGATCTCTCAGGTGGGT | 30.0 | 20.2 |
| *2683 | 35 | AUG | 143–163 | AATCATGACTTCAAGAGTTCT | 47.9 | 48.5 |
| *2686 | 36 | AUG | 148–168 | TGAAGCAATCATGACTTCAAG | 51.1 | 46.9 |
| *4756 | 54 | I/E | 177–196 | CCAAAGTGAGAGCTGAGAGA | 53.9 | 35.7 |
| 4732 | 55 | Coding | 1936–1955 | CTGATTCAAGGCTTTGGCAG | 68.5 | 55.3 |
| *4730 | 56 | I/E 3'UTR | 2006–2025 | TTCCCCAGATGCACCTGTTT | 14.1 | 2.3 |
| *4729 | 57 | 3'-UTR | 2063–2082 | GGGCCAGAGACCCGAGGAGA | 49.4 | 46.3 |
| *2674 | 31 | 3'-UTR | 2617–2637 | CACAATCCTTAAGAACTCTTT | 33.5 | 28.1 |
| 2673 | 30 | 3'-UTR | 2656–2676 | GTATGGAAGATTATAATATAT | 58.9 | 53.8 |
| 2694 | 39 | 3'-UTR | 2933–2953 | GACAATATACAAACCTTCCAT | 72.0 | 64.6 |
| *4719 | 58 | 3'-UTR | 2993–3012 | ACGTTTGGCCTCATGGAAGT | 36.8 | 34.7 |
| 4720 | 59 | 3'-UTR | 3093–3112 | GGAATGCAAAGCACATCCAT | 63.5 | 70.6 |
| *2678 | 32 | 3'-UTR | 3557–3576 | ACCTCTGCTGTTCTGATCCT | 24.9 | 15.3 |
| 2670 | 29 | 3'-UTR | 3717–3736 | ACCACACTGGTATTTCACAC | 72.2 | 67.2 |

I/E indicates Intron/Exon junction
Oligonucleotides with IC$_{50}$'s of approximately 50 nM or below are indicated by an asterisk (*).

Example 10
ELISA screening of antisense oligonucleotides for activity against VCAM-1 gene expression Inhibition of VCAM-1 expression by fifteen antisense phosphorothioate oligonucleotides was determined using the ELISA assay approximately as described in Example 8, except that cells were stimulated with TNF-α for 16 hours and VCAM-1 expression was detected by a VCAM-1 specific monoclonal antibody (R & D Systems, Minneapolis, Minn.) used at 0.5 µg/ml. The sequence and activity of each oligonucleotide against VCAM-1 are shown in Table 4. The oligonucleotides indicated by an asterisk (*) have IC$_{50}$'s of approximately 50 nM or below and are preferred. IC$_{50}$ indicates the dosage of oligonucleotide which results in 50% inhibition of VCAM-1 expression.

Example 11
Murine models for testing antisense oligonucleotides against ICAM-1

Many conditions which are believed to be mediated by intercellular adhesion molecules are not amenable to study in humans. For example, allograft rejection is a condition which is likely to be ameliorated by interference with ICAM-1 expression, but clearly this must be evaluated in animals rather than human transplant patients. These conditions can be tested in animal models, however, such as the mouse models used here.

Oligonucleotide sequences for inhibiting ICAM-1 expression in murine cells were identified. Murine ICAM-1 has approximately 50% homology with the human ICAM-1 sequence; a series of oligonucleotides which target the

TABLE 4

Inhibition of human VCAM-1 expression by antisense oligonucleotides
VCAM-1 expression is given as % of control

| | | | | | VCAM-1 EXPRESSION | |
|---|---|---|---|---|---|---|
| ISIS # | SEQ ID # | POSITION | | SEQUENCE | 30 nM oligo | 50 nM oligo |
| *5884 | 60 | 5'-UTR | 1–19 | CGATGCAGATACCGCGGAGT | 79.2 | 37.2 |
| 3791 | 61 | 5'-UTR | 38–58 | GCCTGGGAGGGTATTCAGCT | 92.6 | 58.0 |
| 5862 | 62 | 5'-UTR | 48–68 | CCTGTGTGTGCCTGGGAGGG | 115.0 | 83.5 |
| *3792 | 63 | AUG | 110–129 | GGCATTTTAAGTTGCTGTCG | 68.7 | 33.7 |
| 5863 | 64 | CODING | 745–764 | CAGCCTGCCTTACTGTGGGC | 95.8 | 66.7 |
| *5874 | 65 | CODING | 1032–1052 | CTTGAACAATTAATTCCACCT | 66.5 | 35.3 |
| 5885 | 66 | E/I | 1633–1649 + intron | TTACCATTGACATAAAGTGTT | 84.4 | 52.4 |
| *5876 | 67 | CODING | 2038–2057 | CTGTGTCTCCTGTCTCCGCT | 43.5 | 26.6 |
| *5875 | 68 | CODING | 2183–2203 | GTCTTTGTTGTTTTCTCTTCC | 59.2 | 34.8 |
| 3794 | 69 | TERMIN. | 2344–2362 | TGAACATATCAAGCATTAGC | 75.3 | 52.6 |
| *3800 | 70 | 3'-UTR | 2620–2639 | GCAATCTTGCTATGGCATAA | 64.4 | 47.7 |
| *3805 | 71 | 3'-UTR | 2826–2845 | CCCGGCATCTTTACAAAACC | 67.7 | 44.9 |
| *3801 | 50 | 3'-UTR | 2872–2892 | AACCCAGTGCTCCCTTTGCT | 36.5 | 21.3 |
| *5847 | 72 | 3'-UTR | 2957–2976 | AACATCTCCGTACCATGCCA | 51.8 | 24.6 |
| *3804 | 51 | 3'-UTR | 3005–3024 | GGCCACATTGGGAAAGTTGC | 55.1 | 29.3 |

E/I indicates exon/intron junction
Oligonucleotides with IC$_{50}$'s of approximately 50 nM or below are indicated by an asterisk (*).

mouse ICAM-1 mRNA sequence were designed and synthesized, using information gained from evaluation of oligonucleotides targeted to human ICAM-1. These oligonucleotides were screened for activity using an immunoprecipitation assay.

Murine DCEK-ICAM-1 cells (a gift from Dr. Adrienne Brian, University of California at San Diego) were treated with 1 μM of oligonucleotide in the presence of 20 μg/ml DOTMA/DOPE solution for 4 hours at 37° C. The medium was replaced with methionine-free medium plus 10% dialyzed fetal calf serum and 1 μM antisense oligonucleotide. The cells were incubated for 1 hour in methionine-free medium, then 100 μCi/ml $^{35}$S-labeled methionine/cysteine mixture was added to the cells. Cells were incubated an additional 2 hours, washed 4 times with PBS, and extracted with buffer containing 20 mM Tris, pH 7.2, 20 mM KCl, 5 mM EDTA, 1% Triton X-100, 0.1 mM leupeptin, 10 μg/ml aprotinin, and 1 mM PMSF. ICAM-1 was immunoprecipitated from the extracts by incubating with a murine-specific ICAM-1 antibody (YN1/1.7.4) followed by protein G-sepharose. The immunoprecipitates were analyzed by SDS-PAGE and autoradiographed. Phosphorothioate oligonucleotides ISIS 3066 and 3069, which target the AUG codon of mouse ICAM-1, inhibited ICAM-1 synthesis by 48% and 63%, respectively, while oligonucleotides ISIS 3065 and ISIS 3082, which target sequences in the 3'-untranslated region of murine ICAM-1 mRNA inhibited ICAM-1 synthesis by 47% and 97%, respectively. The most active antisense oligonucleotide against mouse ICAM-1 was targeted to the 3'-untranslated region. ISIS 3082 was evaluated further based on these results; this 20-mer phosphorothioate oligonucleotide comprises the sequence (5' to 3') TGC ATC CCC CAG GCC ACC AT (SEQ ID NO: 83).

Example 12
Evaluation of ICAM-1 antisense oligonucleotides in bEND.3 murine endothelioma cells bEND.3 cells were provided by Dr. Werner Risau, Max-Planck-Instiutes, Martinsreid, Germany. Cells were treated with oligonucleotide in the presence of 15 μg/ml DOTMA/DOPE liposome formulation for 4 hours. ICAM-1 expression was induced by treatment with 5 ng/ml human rTNF-α and 1000 u/ml murine IFN-γ for 16 hours. Cells were fixed with ethanol and ICAM-1 expression was quantitated by incubating with ICAM-1 monoclonal antibody (YN1/1.7.4, purified from ascites) followed by a biotinylated goat anti-rat IgG antibody and streptavidin-conjugated β-galactosidase. Results are expressed as percent control ICAM-1 expression. Both basal and cytokine-treated cells were pretreated with DOTMA.

Phosphorothioate oligonucleotides ISIS 3068, 3069, 3066, 3070, 3065, 3082, 3806, 3083, 3084 and 3099 were screened by ELISA in the bEND.3 murine endothelioma cell line. These oligonucleotides are shown in Table 5.

TABLE 5

Effect of antisense phosphorothioate oligonucleotides on ICAM-1 expression in bEND.3 cells

| ISIS # | Sequence | | | | | | | % of control expression | SEQ ID NO |
|---|---|---|---|---|---|---|---|---|---|
| 3068 | AGC | TGC | GCT | GCT | ACC | TGC | AC | 25% | 89 |
| 3069 | GCC | CAT | TGC | AGG | GCC | AGG | GC | −5% | 87 |
| 3066 | GGG | TTG | AAG | CCA | TTG | CAG | GG | 45% | 86 |

TABLE 5-continued

Effect of antisense phosphorothioate oligonucleotides on ICAM-1 expression in bEND.3 cells

| ISIS # | Sequence | | | | | | | % of control expression | SEQ ID NO |
|---|---|---|---|---|---|---|---|---|---|
| 3070 | CTC | ATC | CAG | CAG | GCT | CAG | GG | 75% | 90 |
| 3065 | CCA | GAG | GAA | GTG | GCT | GAG | GG | 35% | 88 |
| 3082 | TGC | ATC | CCC | CAG | GCC | ACC | AT | −55% | 83 |
| 3806 | CAA | GTG | TGC | ATC | CCC | CAG | GC | −30% | 91 |
| 3083 | TTG | GGA | CAA | TGT | CTC | AGC | TT | 25% | 92 |
| 3084 | TGC | CAG | TCC | ACA | TAG | TGT | TT | 25% | 93 |
| 3099 | TGC | TTA | CCC | TCC | CAC | AGC | AG | 5% | 94 |

The bEND.3 cells expressed a basal level of ICAM-1 molecules that increased significantly after treatment with a combination of human TNF-α and murine IFN-γ. All of the oligonucleotides inhibited cytokine-induced ICAM-1 expression compared to control, two oligonucleotides, ISIS 3082 and ISIS 3806, lowered ICAM-1 protein expression to below the basal level of expression. ISIS 3082 was also shown to reduce cytokine-induced ICAM-1 mRNA by greater than 95%. This effect was specific. Control oligonucleotide ISIS 7253 (SEQ ID NO: 95, a random mixture of the four bases at each position in a phosphorothioate 20 mer) and unrelated control oligonucleotide ISIS 1082 (SEQ ID NO: 96) did not reduce ICAM-1 mRNA expression.

Example 13
Antisense oligonucleotide to ICAM-1 increases survival in murine heterotopic heart transplant model To determine the therapeutic effects of ICAM-1 antisense oligonucleotide in preventing allograft rejection, the murine ICAM-1 specific oligonucleotide ISIS 3082 was tested for activity in a murine vascularized heterotopic heart transplant model. Hearts from Balb/c mice were transplanted into the abdominal cavity of C3H mice as primary vascularized grafts essentially as described by Isobe et al., *Circulation* 1991, 84, 1246–1255. Oligonucleotides were administered by continuous intravenous administration via a 7-day Alzet pump. The mean survival time for untreated mice was 9.2±0.8 days (8, 9, 9, 9, 10, 10 days). Treatment of the mice for 7 days with 5 mg/kg ISIS 3082 increased the mean survival time to 14.3±4.6 days (11, 12, 13, 21 days).

Example 14
Additional mouse heterotopic heart transplants:

Other donor/recipient combinations were found to give similar results in the cardiac allograft experiments. Untreated C3H(H-2)$^k$ mice rejected C57BL/10(H-2)$^b$ vascularized heart allografts at a mean survival time of 7.7±1.4 days (6, 7, 7, 7, 8, 9, 10 days). A 7-day infusion of the unrelated control oligonucleotide, ISIS 1082, at either 5.0 or 10.0 mg/kg/day did not affect allograft survival (7.1±0.7 days). In contrast, infusion of the ICAM-1 antisense oligonucleotide ISIS 3082 prolonged allograft survival in a dose-dependent fashion: 1.25 mg/kg/day prolonged graft survival to 11.0±0 days; 2.5 mg/kg/day prolonged survival to 12.0±2.7 days (9, 10, 12, 13, 16 days), 5.0 mg/kg/day to 14.1±2.7 days (10, 12, 12, 13, 16, 16, 17, 17 days) ; and 10.0 mg/kg/day to 15.3±5.8 days (12, 12, 13, 24 days). All are p<0.01. Extended 14-day treatment with ISIS 3082 (5 mg/kg/day) further increased graft survival up to as much as 30 days (16, 17, 29, 30; mean=23.0±7.5 days). Similar results were obtained with C57BL/6(H-2$^b$) to BALB/c transplants.

The effectiveness of the immunosuppression was documented by histological examination of the grafts on day 6 after transplantation. Syngeneic C57BL/10 hearts transplanted to C57BL/10 recipients showed mild infiltration with mononuclear cells (10% of the myocardium) compared to normal controls. Heart allografts from untreated recipients displayed strong infiltration with mononuclear cells and neutrophils. This effect was associated with severe necrosis and mineralization that formed a dense band that affected 60% of the epicardium, myocardium and papillary muscles. In contrast, heart allografts from recipients treated with ISIS 3082 (5 mg/kg/day) showed only scattered infiltration with mononuclear cells in 20% of the myocardium. The antisense oligonucleotide targeted to ICAM-1 inhibited infiltration and subsequent destruction of heart allograft tissue by host cells.

Example 15
Antisense oligonucleotide to ICAM-1 combined with monoclonal antibody to LFA-1 increases survival indefinitely in murine heterotopic heart transplant model Monoclonal antibody (MAb-LFA-1) to LFA-1 was obtained from Dr. Yogita, Juntendo University School of Medicine, Tokyo, Japan. C3H recipients of C57 BL/10 hearts were untreated or treated with daily i.p. injection for 7 days of MAb-LFA-1 (50 µg/day) alone or in combination with ISIS 3082 (5.0 mg/kg/day, administered by Alzet osmotic pump for 7 days). Treatment with MAb-LFA-1 alone prolonged allograft survival to 14.3±2.7 days. Combined treatment with MAb-LFA-1 and ISIS 3082 for 7 days resulted in indefinite survival of the heart allografts (>150 days; p<0.001) in all 5 mice so treated. The interaction between two agents (oligonucleotide and immunosuppressant) was assessed by the combination index (CI) method (Chou, T -C. and Talalay, P. *Adv. Enz. Regul.* 1984, 22, 27) for the doses to achieve x % inhibition (days of graft survival):

$$CIx = \frac{D_1 \text{ combined}}{(Dx)_1 \text{ alone}} + \frac{D_2 \text{ combined}}{(Dx)_2 \text{ alone}}$$

for the mutually exclusive case where both drugs have the same or similar modes of action, or the more conservative expression:

$$CIx = \frac{D_1 \text{ combined}}{(Dx)_1 \text{ alone}} + \frac{D_1 \text{ combined}}{(Dx)_2 \text{ alone}} + \frac{(D_1 \text{ combined})(D_2 \text{ combined})}{[(Dx)_1 \text{ alone}][(Dx_2 \text{ alone}]}$$

for the mutually exclusive case, where each drug has a different mode of action. Computer software (Biosoft, Cambridge UK) was used to determine the CI values. A CI of 1 indicates an additive effect, CI<1 indicates a synergistic effect and CI>1 indicates an antagonistic effect.

The CI value calculated for the combination of 5.0 mg/kg/day ISIS 3082 and 50 µg/day anti-LFA-1 monoclonal antibody was 0.001, indicating strong synergism.

Example 16
Antisense oligonucleotide to ICAM-1 combined with monoclonal antibody to LFA-1 induces donor-specific transplantation tolerance Recipients bearing C57BL/10 hearts for 65 days (n=4) were transplanted with donor-type C57BL/10 and third-party BALB/c (H-2$^d$) skin allografts. Induction of transplantation tolerance was demonstrated by permanent acceptance of donor-type skin grafts (>100 days) and acute rejection of third-party grafts in 9.0±0.0 days. Control C3H mice (n=5) rejected C57BL/10 and BALB/c grafts in 9.2±0.8 days and 8.1±0.6 days, respectively. These results indicate that the combination of ICAM-1 antisense oligonucleotide and monoclonal antibody to LFA-1 induces donor-specific transplantation tolerance.

Example 17
Effects of antisense oligonucleotide to ICAM-1 combined with conventional immunosuppressive drugs The interaction of ISIS 3082 with the immunosuppressive agents rapamycin (RAPA), brequinar (BQR), cyclosporine A (CsA) and anti-lymphocyte serum (ALS) was examined. CsA (Sandoz, Basel, Switzerland) dissolved in cremophor (Sigma, St. Louis Mo.) was delivered via jugular venous infusion by a 7-day osmotic pump (Alzet, Palo Alto Calif.). RAPA (Wyeth Ayerst, Rouse Point N.Y.) diluted in 10% Tween 80, 20% N-N-dimethylacetamide and 70% PEG-400 was infused i.v. by 7-day osmotic pump. BQR (DuPont, Wilmington Del.) diluted in distilled water was administered every second day, q.o.d, by oral gavage for 7 days. Rabbit anti-mouse ALS (Accurate, New York, N.Y.) was injected once i.p. two days before grafting.

These immunosuppressive modalities act in different ways: ALS decreases the level of T cells, including the alloantigen-specific T cells. Monaco et al., *J. Immunol.* 1966, 96, 229–238. RAPA inhibits the transduction of signals delivered by lymphokines (Morice et al., *J. Biol. Chem.* 1993, 268, 3734–3738) and BQR blocks the dihydroorotate dehydrogenase enzyme that is required for pyrimidine synthesis [Chen et al., *Cancer Res.* 1986, 46, 5014–5020]. CsA blocks calcineurin activity, thereby inhibiting the synthesis of lymphokines by T cells. Liu et al., *Cell* 1991, 66, 807–815.

A single i.p. injection of ALS alone two days prior to transplantation prolonged graft survival in a dose-dependent manner: 0.1 ml gave a mean survival of 9.0±0.0 days; 0.2 ml gave a mean of 10.4±0.5 days (10, 10, 10, 11, 11 days) and 0.4 ml gave a mean survival of 14.0±2.1 days (11, 14, 15, 16 days). All are p<0.01. The combination of 0.2 ml ALS and the antisense oligonucleotide ISIS 3082 extended allograft survivals to 32.2±8.3 days (20, 30, 31, 39, 41 days), 37.0±5.8 days (32, 32, 41, 43 days) and 72.0±49.1 days (33, 34, 54, 89, >150 days), respectively. All are p<0.01 and CI<0.001.

RAPA alone (0.05, 0.1 or 0.2 mg/kg/day) delivered i.v. by a 7-day osmotic pump prolonged graft survival in a dose-dependent manner: 0.05 mg/kg/day gave a mean survival of 7.4±1.4 days (6, 6, 7, 9, 9 days); 0.1 mg/kg/day gave a mean survival of 13.0±7.5 days (10, 11, 20, 20, 21 days) and 0.2 mg/kg/day gave a mean survival of 20.0±10.9 days (12, 14, 17, 18, 39 days). The combination of 0.1 mg/kg/day RAPA and the antisense oligonucleotide ISIS 3082 extended allograft survivals to 32.4±8.9 days (23, 24, 33, 39, 43 days) at 5 mg/kg/day of ISIS 3082 and 36.3±6.1 days (32, 32, 36, 45 days) at 10 mg/kg/day of ISIS 3082. Both are p<0.01 and CI<0.02.

Oral gavage with BQR alone (0.5, 1.0 or 2.0 mg/kg/day) delivered every second day (q.o.d.) for 7 days prolonged allograft survival to 12.0±2.4 days (9, 11, 11, 14, 15 days), 17.6 days (13, 16, 18, 19, 22 days) or 20.0±4.1 days (15, 17, 20, 23, 25 days), respectively. The combination of 0.5 mg/kg BQR and 5.0 mg/kg ISIS 3082 resulted in a mean survival time of 38.8±30.2 days (21, 24, 28, 28, 31, >100) (p<0.01; CI=0.007).

A 7-day i.v. infusion of CsA, 2.5 or 5.0 mg/kg/day, was ineffective; 10.0 or 20.0 mg/kg/day CsA did prolong allograft survival. Addition of ISIS 3082 (5.0 or 10.0 mg/kg/day) to CsA treatment (5.0 mg/kg/day) did not improve graft survival. CI was 14.1 and 51.0, respectively. A combination of the control oligonucleotide, ISIS 1082, and CsA did not affect graft survival time.

These results show that the ICAM-1 antisense oligonucleotide ISIS 3082 interacts synergistically with the immunosuppressive agents ALS, RAPA and BQR, but not with CsA, to block allograft rejection. Because CsA is not very effective in mice, it is unclear whether the lack of synergism between the antisense oligonucleotide and CsA is a pharmacological or a pharmacokinetic effect.

Example 18

Toxicology and pharmacokinetics of ISIS 3082

The ICAM-1 antisense oligonucleotide ISIS 3082 was well tolerated at therapeutic doses without producing signs of toxicity. Even at high doses (100.0 mg/kg/day given q.o.d for 14 days), ISIS 3082 did not produce any major side effects and did not induce an antigenic response.

Interestingly, ISIS 3082 was shown to be active in prolonging heart allograft survival when delivered in a saline suspension, without cationic liposomes. Similar observations have been made with other phosphorothioate oligonucleotides directed at other targets (see, for example, Simons et al., Nature 1992, 359, 67–70; Kitajima et al., Science 1992, 258, 1792–1795). Thus, although cationic liposomes enhance the effect of many oligonucleotides, including ISIS 3082, in vitro, they are not necessarily required for efficacy of the same oligonucleotides in vivo.

What is claimed is:

1. A composition for treating allograft rejection comprising an oligonucleotide targeted to a nucleic acid sequence encoding intercellular adhesion molecule-1, endothelial leukocyte adhesion molecule-1 or vascular cell adhesion molecule-1 in combination with an immunosuppressive agent, said oligonucleotide consisting of SEQ ID NO: 1, 7, 8, 13, 14, 15, 22, 23, 24, 25, 26, 84, 31, 32, 33, 35, 36, 52, 53, 54, 56, 57, 58, 50, 51, 60, 63, 65, 67, 68, 70, 71 or 72.

2. The composition of claim 1 wherein the oligonucleotide comprises SEQ ID NO: 22.

3. The composition of claim 1 wherein the immunosuppressive agent is a monoclonal antibody directed against lymphocyte function associated antigen-1.

4. The composition of claim 1 wherein the immunosuppressive agent is brequinar, rapamycin or anti-lymphocyte serum.

5. The composition of claim 1 wherein the immunosuppressive agent is an antisense oligonucleotide targeted to B7-2 or LFA-1.

6. A method of treating allograft rejection in an allograft recipient comprising treating the allograft recipient with a composition of claim 1.

7. A method of preventing allograft rejection in an allograft recipient comprising treating the allograft recipient with an oligonucleotide targeted to a nucleic acid sequence encoding intercellular adhesion molecule-1, endothelial leukocyte adhesion molecule-1 or vascular cell adhesion molecule-1, in combination with an immunosuppressive agent, said oligonucleotide consisting of SEQ ID NO: 1, 7, 8, 13, 14, 15, 22, 23, 24, 25, 26, 84, 31, 32, 33, 35, 36, 52, 53, 54, 56, 57, 58, 50, 51, 60, 63, 65, 67, 68, 70, 71 or 72.

8. The method of claim 7 wherein the immunosuppressive agent is a monoclonal antibody directed against lymphocyte function associated antigen-1.

9. The method of claim 7 wherein the immunosuppressive agent is brequinar, rapamycin or anti-lymphocyte serum.

10. The method of claim 7 wherein the immunosuppressive agent is an antisense oligonucleotide targeted to B7-2 or LFA-1.

11. The method of claim 7 wherein the allograft is a cardiac allograft.

12. The method of claim 7 wherein the allograft is a renal allograft.

13. A method of preventing allograft rejection in an allograft recipient comprising treating the allograft recipient with a composition of claim 1.

14. A method of preventing rejection of an allograft by an allograft recipient comprising perfusing the allograft with a composition of claim 1.

15. The method of claim 14 wherein the perfusion is performed ex vivo.

16. A method of preventing rejection of an allograft comprising perfusing the allograft with an oligonucleotide targeted to a nucleic acid sequence encoding intercellular adhesion molecule-1, endothelial leukocyte adhesion molecule-1 or vascular cell adhesion molecule-1, said oligonucleotide consisting of SEQ ID NO: 1, 7, 8, 13, 14, 15, 22, 23, 24, 25, 26, 84, 31, 32, 33, 35, 36, 52, 53, 54, 56, 57, 58, 50, 51, 60, 63, 65, 67, 68, 70, 71 or 72.

17. The method of claim 16 wherein the oligonucleotide comprises SEQ ID NO: 22.

18. A method of treating allograft rejection in an allograft recipient comprising treating the allograft recipient with an oligonucleotide targeted to a nucleic acid sequence encoding intercellular adhesion molecule-1, endothelial leukocyte adhesion molecule-1 or vascular cell adhesion molecule-1 in combination with an immunosuppressive agent, said oligonucleotide consisting of SEQ ID NO: 1, 7, 8, 13, 14, 15, 22, 23, 24, 25, 26, 84, 31, 32, 33, 35, 36, 52, 53, 54, 56, 57, 58, 50, 51, 60, 63, 65, 67, 68, 70, 71 or 72.

19. The method of claim 18 wherein the immunosuppressive agent is a monoclonal antibody directed against lymphocyte function associated antigen-1.

20. The method of claim 18 wherein the immunosuppressive agent is brequinar, rapamycin or anti-lymphocyte serum.

21. The method of claim 18 wherein the immunosuppressive agent is an antisense oligonucleotide targeted to B7-2 or LFA-1.

22. The method of claim 18 wherein the allograft is a cardiac allograft.

23. The method of claim 18 wherein the allograft is a renal allograft.

* * * * *

UNITED STATES PATENT AND TRADEMARK OFFICE
CERTIFICATE OF CORRECTION

PATENT NO. : 5,883,082
DATED : March 16, 1999
INVENTOR(S) : Bennett et al.

It is certified that error appears in the above-identified patent and that said Letters Patent is hereby corrected as shown below:

At col 13, line 21, (Table 1), please delete "P=s" and insert therefor --P=S--.

At col 16, line 3, please delete "1 hour at 20 37°C" and insert therefor --1 hour at 37°C--.

At col 16, line 28 (Table 2), please delete "P=s" and insert therefor --P=S--.

At col. 16, lines 58-59 please delete "(*) IC50's" and insert therefor --(*) have IC50's--.

At col 16, line 63, please delete "4723" and insert therefor --4728--.

Signed and Sealed this

Twenty-eighth Day of March, 2000

Attest:

Q. TODD DICKINSON

*Attesting Officer*    *Commissioner of Patents and Trademarks*

SEQUENCE LISTING ( 1 ) GENERAL INFORMATION:

( i i i ) NUMBER OF SEQUENCES: 99

( 2 ) INFORMATION FOR SEQ ID NO:1:

( i ) SEQUENCE CHARACTERISTICS:
        ( A ) LENGTH: 18
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 1:

TGGGAGCCAT AGCGAGGC                                        1 8

( 2 ) INFORMATION FOR SEQ ID NO: 2:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 2:

GAGGAGCTCA GCGTCGACTG                                    2 0

( 2 ) INFORMATION FOR SEQ ID NO: 3:

( i ) SEQUENCE CHARACTERISTICS:
        ( A ) LENGTH: 21
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 3:

GACACTCAAT AAATAGCTGG T                                   2 1

( 2 ) INFORMATION FOR SEQ ID NO: 4:

( i ) SEQUENCE CHARACTERISTICS:
        ( A ) LENGTH: 18
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 4:

GAGGCTGAGG TGGGAGGA                                                                                                         18

( 2 ) INFORMATION FOR SEQ ID NO: 5:

( i ) SEQUENCE CHARACTERISTICS:
           ( A ) LENGTH: 18
           ( B ) TYPE: Nucleic Acid
           ( C ) STRANDEDNESS: Single
           ( D ) TOPOLOGY: Linear ( i v ) ANTI-SENSE: Yes ( x i ) SEQUENCE DESCRIPTION: SEQ ID NO: 5:

CGATGGGCAG TGGGAAAG                                                                                                         18

( 2 ) INFORMATION FOR SEQ ID NO: 6:

( i ) SEQUENCE CHARACTERISTICS:
           ( A ) LENGTH: 20
           ( B ) TYPE: Nucleic Acid
           ( C ) STRANDEDNESS: Single
           ( D ) TOPOLOGY: Linear ( i v ) ANTI-SENSE: Yes ( x i ) SEQUENCE DESCRIPTION: SEQ ID NO: 6:

GGGCGCGTGA TCCTTATAGC                                                                                                       20

( 2 ) INFORMATION FOR SEQ ID NO: 7:

( i ) SEQUENCE CHARACTERISTICS:
           ( A ) LENGTH: 20
           ( B ) TYPE: Nucleic Acid
           ( C ) STRANDEDNESS: Single
           ( D ) TOPOLOGY: Linear ( i v ) ANTI-SENSE: Yes ( x i ) SEQUENCE DESCRIPTION: SEQ ID NO: 7:

CATAGCGAGG CTGAGGTTGC                                                                                                       20

( 2 ) INFORMATION FOR SEQ ID NO: 8:

( i ) SEQUENCE CHARACTERISTICS:
           ( A ) LENGTH: 20
           ( B ) TYPE: Nucleic Acid
           ( C ) STRANDEDNESS: Single
           ( D ) TOPOLOGY: Linear ( i v ) ANTI-SENSE: Yes ( x i ) SEQUENCE DESCRIPTION: SEQ ID NO: 8:

CGGGGGCTGC TGGGAGCCAT                                                                                                       20

( 2 ) INFORMATION FOR SEQ ID NO: 9:

( i ) SEQUENCE CHARACTERISTICS:
           ( A ) LENGTH: 20
           ( B ) TYPE: Nucleic Acid
           ( C ) STRANDEDNESS: Single
           ( D ) TOPOLOGY: Linear ( i v ) ANTI-SENSE: Yes ( x i ) SEQUENCE DESCRIPTION: SEQ ID NO: 9:

AGAGCCCCGA GCAGGACCAG                                                                                                       20

(2) INFORMATION FOR SEQ ID NO: 10:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 10:

TGCCCATCAG GGCAGTTTGA　　　　　　　　　　　　　　　　　　　　　　　　　20

(2) INFORMATION FOR SEQ ID NO: 11:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 11:

GGTCACACTG ACTGAGGCCT　　　　　　　　　　　　　　　　　　　　　　　　　20

(2) INFORMATION FOR SEQ ID NO: 12:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 12:

CTCGCGGGTG ACCTCCCCTT　　　　　　　　　　　　　　　　　　　　　　　　　20

(2) INFORMATION FOR SEQ ID NO: 13:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 13:

TCAGGGAGGC GTGGCTTGTG　　　　　　　　　　　　　　　　　　　　　　　　　20

(2) INFORMATION FOR SEQ ID NO: 14:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 14:

CCTGTCCCGG GATAGGTTC A　　　　　　　　　　　　　　　　　　　　　　　　20

(2) INFORMATION FOR SEQ ID NO: 15:

(i) SEQUENCE CHARACTERISTICS:
        (A) LENGTH: 20
        (B) TYPE: Nucleic Acid (C) STRANDEDNESS: Single
(D) TOPOLOGY: Linear (iv) ANTI-SENSE: Yes (xi) SEQUENCE DESCRIPTION: SEQ ID NO: 15:

CCCCCACCAC TTCCCCTCTC 20

(2) INFORMATION FOR SEQ ID NO: 16:

(i) SEQUENCE CHARACTERISTICS:
(A) LENGTH: 20
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 16:

TTGAGAAAGC TTTATTAACT 20

(2) INFORMATION FOR SEQ ID NO: 17:

(i) SEQUENCE CHARACTERISTICS:
(A) LENGTH: 14
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 17:

AGCCATAGCG AGGC 14

(2) INFORMATION FOR SEQ ID NO: 18:

(i) SEQUENCE CHARACTERISTICS:
(A) LENGTH: 12
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 18:

CCATAGCGAG GC 12

(2) INFORMATION FOR SEQ ID NO: 19:

(i) SEQUENCE CHARACTERISTICS:
(A) LENGTH: 10
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 19:

ATAGCGAGGC 10

(2) INFORMATION FOR SEQ ID NO: 20:

(i) SEQUENCE CHARACTERISTICS:
(A) LENGTH: 16
(B) TYPE: Nucleic Acid
(C) STRANDEDNESS: Single
(D) TOPOLOGY: Linear (iv) ANTI-SENSE: Yes ( x i ) SEQUENCE DESCRIPTION: SEQ ID NO: 20:

TGGGAGCCAT AGCGAG 16

( 2 ) INFORMATION FOR SEQ ID NO: 21:

( i ) SEQUENCE CHARACTERISTICS:
        ( A ) LENGTH: 16
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 21:

GGAGCCATAG CGAGGC 16

( 2 ) INFORMATION FOR SEQ ID NO: 22:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 22:

GCCCAAGCTG GCATCCGTCA 20

( 2 ) INFORMATION FOR SEQ ID NO: 23:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 23:

TCTGTAAGTC TGTGGGCCTC 20

( 2 ) INFORMATION FOR SEQ ID NO: 24:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 24:

AGTCTTGCTC CTTCCTCTTG 20

( 2 ) INFORMATION FOR SEQ ID NO: 25:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 25:

CTCATCAGGC TAGACTTTAA 20

( 2 ) INFORMATION FOR SEQ ID NO: 26:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 26:

TGTCCTCATG GTGGGGCTAT     20

( 2 ) INFORMATION FOR SEQ ID NO: 27:

( i ) SEQUENCE CHARACTERISTICS:
    ( A ) LENGTH: 22
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 27:

TCTGAGTAGC AGAGGAGCTC GA     22

( 2 ) INFORMATION FOR SEQ ID NO: 28:

( i ) SEQUENCE CHARACTERISTICS:
    ( A ) LENGTH: 22
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 28:

CAATCATGAC TTCAAGAGTT CT     22

( 2 ) INFORMATION FOR SEQ ID NO: 29:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 29:

ACCACACTGG TATTTCACAC     20

( 2 ) INFORMATION FOR SEQ ID NO: 30:

( i ) SEQUENCE CHARACTERISTICS:
    ( A ) LENGTH: 21
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 30:

GTATGGAAGA TTATAATATA T     21

( 2 ) INFORMATION FOR SEQ ID NO: 31:

( i ) SEQUENCE CHARACTERISTICS:
    ( A ) LENGTH: 21
    ( B ) TYPE: Nucleic Acid ( C ) STRANDEDNESS: Single
            ( D ) TOPOLOGY: Linear ( i v ) ANTI-SENSE: Yes ( x i ) SEQUENCE DESCRIPTION: SEQ ID NO: 31:

CACAATCCTT AAGAACTCTT T                                        21

( 2 ) INFORMATION FOR SEQ ID NO: 32:

( i ) SEQUENCE CHARACTERISTICS:
            ( A ) LENGTH: 20
            ( B ) TYPE: Nucleic Acid
            ( C ) STRANDEDNESS: Single
            ( D ) TOPOLOGY: Linear ( i v ) ANTI-SENSE: Yes ( x i ) SEQUENCE DESCRIPTION: SEQ ID NO: 32:

ACCTCTGCTG TTCTGATCCT                                          20

( 2 ) INFORMATION FOR SEQ ID NO: 33:

( i ) SEQUENCE CHARACTERISTICS:
            ( A ) LENGTH: 20
            ( B ) TYPE: Nucleic Acid
            ( C ) STRANDEDNESS: Single
            ( D ) TOPOLOGY: Linear ( i v ) ANTI-SENSE: Yes ( x i ) SEQUENCE DESCRIPTION: SEQ ID NO: 33:

CTGCTGCCTC TGTCTCAGGT                                          20

( 2 ) INFORMATION FOR SEQ ID NO: 34:

( i ) SEQUENCE CHARACTERISTICS:
            ( A ) LENGTH: 15
            ( B ) TYPE: Nucleic Acid
            ( C ) STRANDEDNESS: Single
            ( D ) TOPOLOGY: Linear ( i v ) ANTI-SENSE: Yes ( x i ) SEQUENCE DESCRIPTION: SEQ ID NO: 34:

GGTATTTGAC ACAGC                                               15

( 2 ) INFORMATION FOR SEQ ID NO: 35:

( i ) SEQUENCE CHARACTERISTICS:
            ( A ) LENGTH: 21
            ( B ) TYPE: Nucleic Acid
            ( C ) STRANDEDNESS: Single
            ( D ) TOPOLOGY: Linear ( i v ) ANTI-SENSE: Yes ( x i ) SEQUENCE DESCRIPTION: SEQ ID NO: 35:

AATCATGACT TCAAGAGTTC T                                        21

( 2 ) INFORMATION FOR SEQ ID NO: 36:

( i ) SEQUENCE CHARACTERISTICS:
            ( A ) LENGTH: 21
            ( B ) TYPE: Nucleic Acid
            ( C ) STRANDEDNESS: Single
            ( D ) TOPOLOGY: Linear ( i v ) ANTI-SENSE: Yes ( x i ) SEQUENCE DESCRIPTION: SEQ ID NO: 36:

TGAAGCAATC ATGACTTCAA G 21

( 2 ) INFORMATION FOR SEQ ID NO: 37:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 37:

TATAGGAGTT TTGATGTGAA 20

( 2 ) INFORMATION FOR SEQ ID NO: 38:

( i ) SEQUENCE CHARACTERISTICS:
        ( A ) LENGTH: 21
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 38:

ACAATGAGGG GGTAATCTAC A 21

( 2 ) INFORMATION FOR SEQ ID NO: 39:

( i ) SEQUENCE CHARACTERISTICS:
        ( A ) LENGTH: 21
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 39:

GACAATATAC AAACCTTCCA T 21

( 2 ) INFORMATION FOR SEQ ID NO: 40:

( i ) SEQUENCE CHARACTERISTICS:
        ( A ) LENGTH: 21
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 40:

CCAGGCATTT TAAGTTGCTG T 21

( 2 ) INFORMATION FOR SEQ ID NO: 41:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 41:

CCTGAAGCCA GTGAGGCCCG 20

( 2 ) INFORMATION FOR SEQ ID NO: 42:

( i ) SEQUENCE CHARACTERISTICS:
        ( A ) LENGTH: 21
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 42:

GATGAGAAAA TAGTGGAACC A        21

( 2 ) INFORMATION FOR SEQ ID NO: 43:

( i ) SEQUENCE CHARACTERISTICS:
        ( A ) LENGTH: 19
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 43:

CTGAGCAAGA TATCTAGAT        19

( 2 ) INFORMATION FOR SEQ ID NO: 44:

( i ) SEQUENCE CHARACTERISTICS:
        ( A ) LENGTH: 19
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 44:

CTACACTTTT GATTTCTGT        19

( 2 ) INFORMATION FOR SEQ ID NO: 45:

( i ) SEQUENCE CHARACTERISTICS:
        ( A ) LENGTH: 22
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 45:

TTGAACATAT CAAGCATTAG CT        22

( 2 ) INFORMATION FOR SEQ ID NO: 46:

( i ) SEQUENCE CHARACTERISTICS:
        ( A ) LENGTH: 22
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 46:

TTTACATATG TACAAATTAT GT        22

( 2 ) INFORMATION FOR SEQ ID NO: 47:

( i ) SEQUENCE CHARACTERISTICS:
        ( A ) LENGTH: 22
        ( B ) TYPE: Nucleic Acid ( C ) STRANDEDNESS: Single
( D ) TOPOLOGY: Linear ( i v ) ANTI-SENSE: Yes ( x i ) SEQUENCE DESCRIPTION: SEQ ID NO: 47:

AATTATCACT TTACTATACA AA 22

( 2 ) INFORMATION FOR SEQ ID NO: 48:

( i ) SEQUENCE CHARACTERISTICS:
( A ) LENGTH: 21
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 48:

AGGGCTGACC AAGACGGTTG T 21

( 2 ) INFORMATION FOR SEQ ID NO: 49:

( i ) SEQUENCE CHARACTERISTICS:
( A ) LENGTH: 20
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 49:

CCATCTTCCC AGGCATTTTA 20

( 2 ) INFORMATION FOR SEQ ID NO: 50:

( i ) SEQUENCE CHARACTERISTICS:
( A ) LENGTH: 20
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 50:

AACCCAGTGC TCCCTTTGCT 20

( 2 ) INFORMATION FOR SEQ ID NO: 51:

( i ) SEQUENCE CHARACTERISTICS:
( A ) LENGTH: 20
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 51:

GGCCACATTG GGAAAGTTGC 20

( 2 ) INFORMATION FOR SEQ ID NO: 52:

( i ) SEQUENCE CHARACTERISTICS:
( A ) LENGTH: 20
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 52:

GAAGTCAGCC AAGAACAGCT 20

( 2 ) INFORMATION FOR SEQ ID NO: 53:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 53:

ACAGGATCTC TCAGGTGGGT 20

( 2 ) INFORMATION FOR SEQ ID NO: 54:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 54:

CCAAAGTGAG AGCTGAGAGA 20

( 2 ) INFORMATION FOR SEQ ID NO: 55:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 55:

CTGATTCAAG GCTTTGGCAG 2

( 2 ) INFORMATION FOR SEQ ID NO: 56:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 56:

TTCCCCAGAT GCACCTGTTT 20

( 2 ) INFORMATION FOR SEQ ID NO: 57:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 57:

GGGCCAGAGA CCCGAGGAGA 20

( 2 ) INFORMATION FOR SEQ ID NO: 58:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 58:

ACGTTTGGCC TCATGGAAGT 20

( 2 ) INFORMATION FOR SEQ ID NO: 59:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 59:

GGAATGCAAA GCACATCCAT 20

( 2 ) INFORMATION FOR SEQ ID NO: 60:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 60:

CGATGCAGAT ACCGCGGAGT 20

( 2 ) INFORMATION FOR SEQ ID NO: 61:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 61:

GCCTGGGAGG GTATTCAGCT 20

( 2 ) INFORMATION FOR SEQ ID NO: 62:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 62:

CCTGTGTGTG CCTGGGAGGG 20

( 2 ) INFORMATION FOR SEQ ID NO: 63:

( i ) SEQUENCE CHARACTERISTICS:
        ( A ) LENGTH: 20
        ( B ) TYPE: Nucleic Acid (C) STRANDEDNESS: Single
(D) TOPOLOGY: Linear (iv) ANTI-SENSE: Yes (xi) SEQUENCE DESCRIPTION: SEQ ID NO: 63:

GGCATTTTAA GTTGCTGTCG 20

(2) INFORMATION FOR SEQ ID NO: 64:

(i) SEQUENCE CHARACTERISTICS:
(A) LENGTH: 20
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 64:

CAGCCTGCCT TACTGTGGGC 20

(2) INFORMATION FOR SEQ ID NO: 65:

(i) SEQUENCE CHARACTERISTICS:
(A) LENGTH: 21
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 65:

CTTGAACAAT TAATTCCACC T 21

(2) INFORMATION FOR SEQ ID NO: 66:

(i) SEQUENCE CHARACTERISTICS:
(A) LENGTH: 21
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 66:

TTACCATTGA CATAAAGTGT T 21

(2) INFORMATION FOR SEQ ID NO: 67:

(i) SEQUENCE CHARACTERISTICS:
(A) LENGTH: 20
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 67:

CTGTGTCTCC TGTCTCCGCT 20

(2) INFORMATION FOR SEQ ID NO: 68:

(i) SEQUENCE CHARACTERISTICS:
(A) LENGTH: 21
(B) TYPE: Nucleic Acid
(C) STRANDEDNESS: Single
(D) TOPOLOGY: Linear (iv) ANTI-SENSE: Yes ( x i ) SEQUENCE DESCRIPTION: SEQ ID NO: 68:

GTCTTTGTTG TTTTCTCTTC C 21

( 2 ) INFORMATION FOR SEQ ID NO: 69:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 69:

TGAACATATC AAGCATTAGC 20

( 2 ) INFORMATION FOR SEQ ID NO: 70:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 70:

GCAATCTTGC TATGGCATAA 20

( 2 ) INFORMATION FOR SEQ ID NO: 71:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 71:

CCCGGCATCT TTACAAAACC 20

( 2 ) INFORMATION FOR SEQ ID NO: 72:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 72:

AACATCTCCG TACCATGCCA 20

( 2 ) INFORMATION FOR SEQ ID NO: 73:

( i ) SEQUENCE CHARACTERISTICS:
        ( A ) LENGTH: 22
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 73:

TCACTGCTGC CTCTGTCTCA GG 22

( 2 ) INFORMATION FOR SEQ ID NO: 74:

( i ) SEQUENCE CHARACTERISTICS:
        ( A ) LENGTH: 23
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 74:

TGATTCTTTT GAACTTAAAA GGA                      23

( 2 ) INFORMATION FOR SEQ ID NO: 75:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 75:

TTAAAGGATG TAAGAAGGCT                        20

( 2 ) INFORMATION FOR SEQ ID NO: 76:

( i ) SEQUENCE CHARACTERISTICS:
        ( A ) LENGTH: 19
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 76:

CATAAGCACA TTTATTGTC                         19

( 2 ) INFORMATION FOR SEQ ID NO: 77:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 77:

TTTTGGGAAG CAGTTGTTCA                        20

( 2 ) INFORMATION FOR SEQ ID NO: 78:

( i ) SEQUENCE CHARACTERISTICS:
        ( A ) LENGTH: 21
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 78:

AACTGTGAAG CAATCATGAC T                      21

( 2 ) INFORMATION FOR SEQ ID NO: 79:

( i ) SEQUENCE CHARACTERISTICS:
        ( A ) LENGTH: 22
        ( B ) TYPE: Nucleic Acid ( C ) STRANDEDNESS: Single
( D ) TOPOLOGY: Linear ( i v ) ANTI-SENSE: Yes ( x i ) SEQUENCE DESCRIPTION: SEQ ID NO: 79:

CCTTGAGTGG TGCATTCAAC CT 22

( 2 ) INFORMATION FOR SEQ ID NO: 80:

( i ) SEQUENCE CHARACTERISTICS:
( A ) LENGTH: 22
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 80:

AATGCTTGCT CACACAGGCA TT 22

( 2 ) INFORMATION FOR SEQ ID NO: 81:

( i ) SEQUENCE CHARACTERISTICS:
( A ) LENGTH: 18
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 81:

GCCTCGCTAT GGCTCCCA 18

( 2 ) INFORMATION FOR SEQ ID NO: 82:

( i ) SEQUENCE CHARACTERISTICS:
( A ) LENGTH: 18
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 82:

CATGGCGCGG GCCGCGGG 18

( 2 ) INFORMATION FOR SEQ ID NO: 83:

( i ) SEQUENCE CHARACTERISTICS:
( A ) LENGTH: 20
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 83:

TGCATCCCCC AGGCCACCAT 20

( 2 ) INFORMATION FOR SEQ ID NO: 84:

( i ) SEQUENCE CHARACTERISTICS:
( A ) LENGTH: 20
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 84:

TCTGAGTAGC AGAGGAGCTC                                           20

( 2 ) INFORMATION FOR SEQ ID NO: 85:

( i ) SEQUENCE CHARACTERISTICS:
　　　　　　　( A ) LENGTH: 20
　　　　　　　( B ) TYPE: Nucleic Acid
　　　　　　　( C ) STRANDEDNESS: Single
　　　　　　　( D ) TOPOLOGY: Linear ( i v ) ANTI-SENSE: Yes ( x i ) SEQUENCE DESCRIPTION: SEQ ID NO: 85:

TATGTCTCCC CCACCACTTC                                           20

( 2 ) INFORMATION FOR SEQ ID NO: 86:

( i ) SEQUENCE CHARACTERISTICS:
　　　　　　　( A ) LENGTH: 20
　　　　　　　( B ) TYPE: Nucleic Acid
　　　　　　　( C ) STRANDEDNESS: Single
　　　　　　　( D ) TOPOLOGY: Linear ( i v ) ANTI-SENSE: Yes ( x i ) SEQUENCE DESCRIPTION: SEQ ID NO: 86:

GGGTTGAAGC CATTGCAGGG                                           20

( 2 ) INFORMATION FOR SEQ ID NO: 87:

( i ) SEQUENCE CHARACTERISTICS:
　　　　　　　( A ) LENGTH: 20
　　　　　　　( B ) TYPE: Nucleic Acid
　　　　　　　( C ) STRANDEDNESS: Single
　　　　　　　( D ) TOPOLOGY: Linear ( i v ) ANTI-SENSE: Yes ( x i ) SEQUENCE DESCRIPTION: SEQ ID NO: 87:

GCCCATTGCA GGGCCAGGGC                                           20

( 2 ) INFORMATION FOR SEQ ID NO: 88:

( i ) SEQUENCE CHARACTERISTICS:
　　　　　　　( A ) LENGTH: 20
　　　　　　　( B ) TYPE: Nucleic Acid
　　　　　　　( C ) STRANDEDNESS: Single
　　　　　　　( D ) TOPOLOGY: Linear ( i v ) ANTI-SENSE: Yes ( x i ) SEQUENCE DESCRIPTION: SEQ ID NO: 88:

CCAGAGGAAG TGGCTGAGGG                                           20

( 2 ) INFORMATION FOR SEQ ID NO: 89:

( i ) SEQUENCE CHARACTERISTICS:
　　　　　　　( A ) LENGTH: 20
　　　　　　　( B ) TYPE: Nucleic Acid
　　　　　　　( C ) STRANDEDNESS: Single
　　　　　　　( D ) TOPOLOGY: Linear ( i v ) ANTI-SENSE: Yes ( x i ) SEQUENCE DESCRIPTION: SEQ ID NO: 89:

AGCTGCGCTG CTACCTGCAC                                           20

( 2 ) INFORMATION FOR SEQ ID NO: 90:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 90:

CTCATCCAGC AGGCTCAGGG　　　　　　　　　　　　　　　　　　　　　　　　　　　20

( 2 ) INFORMATION FOR SEQ ID NO: 91:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 91:

CAAGTGTGCA TCCCCCAGGC　　　　　　　　　　　　　　　　　　　　　　　　　　　20

( 2 ) INFORMATION FOR SEQ ID NO: 92:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 92:

TTGGGACAAT GTCTCAGCTT　　　　　　　　　　　　　　　　　　　　　　　　　　　20

( 2 ) INFORMATION FOR SEQ ID NO: 93:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 93:

TGCCAGTCCA CATAGTGTTT　　　　　　　　　　　　　　　　　　　　　　　　　　　20

( 2 ) INFORMATION FOR SEQ ID NO: 94:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 94:

TGCTTACCCT CCCACAGCAG　　　　　　　　　　　　　　　　　　　　　　　　　　　20

( 2 ) INFORMATION FOR SEQ ID NO: 95:

( i ) SEQUENCE CHARACTERISTICS:
        ( A ) LENGTH: 20
        ( B ) TYPE: Nucleic Acid (C) STRANDEDNESS: Single
(D) TOPOLOGY: Linear (iv) ANTI-SENSE: Yes (xi) SEQUENCE DESCRIPTION: SEQ ID NO: 95:

NNNNNNNNNN NNNNNNNNNN                                                                                           20

(2) INFORMATION FOR SEQ ID NO: 96:

(i) SEQUENCE CHARACTERISTICS:
(A) LENGTH: 21
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 96:

GCCGAGGTCC ATGTCGTACG C                                                                                         21

(2) INFORMATION FOR SEQ ID NO: 97:

(i) SEQUENCE CHARACTERISTICS:
(A) LENGTH: 3016
(B) TYPE: Nucleic Acid
(C) STRANDEDNESS: Single
(D) TOPOLOGY: Linear (iv) ANTI-SENSE: No (xi) SEQUENCE DESCRIPTION: SEQ ID NO: 97:

| GCTATAAGGA | TCACGCGCCC | CAGTCGACGC | TGAGCTCCTC | TGCTACTCAG | | | | | | | | | | | 50 |
|---|---|---|---|---|---|---|---|---|---|---|---|---|---|---|---|
| AGTTGCAACC | TCAGCCTCGC | T | ATG | GCT | CCC | | | | | | | | | | 80 |
|  |  |  | MET | ALA | PRO | | | | | | | | | | |
| AGC | AGC | CCC | CGG | CCC | GCG | CTG | CCC | GCA | CTC | CTG | GTC | CTG | CTC | GGG | 125 |
| SER | SER | PRO | ARG | PRO | ALA | LEU | PRO | ALA | LEU | LEU | VAL | LEU | LEU | GLY |  |
|  | 5 |  |  |  |  | 10 |  |  |  |  | 15 |  |  |  |  |
| GCT | CTG | TTC | CCA | GGA | CCT | GGC | AAT | GCC | CAG | ACA | TCT | GTG | TCC | CCC | 170 |
| ALA | LEU | PHE | PRO | GLY | PRO | GLY | ASN | ALA | GLN | THR | SER | VAL | SER | PRO |  |
|  | 20 |  |  |  |  | 25 |  |  |  |  | 30 |  |  |  |  |
| TCA | AAA | GTC | ATC | CTG | CCC | CGG | GGA | GGC | TCC | GTG | CTG | GTG | ACA | TGC | 215 |
| SER | LYS | VAL | ILE | LEU | PRO | ARG | GLY | GLY | SER | VAL | LEU | VAL | THR | CYS |  |
|  | 35 |  |  |  |  | 40 |  |  |  |  | 45 |  |  |  |  |
| AGC | ACC | TCC | TGT | GAC | CAG | CCC | AAG | TTG | TTG | GGC | ATA | GAG | ACC | CCG | 260 |
| SER | THR | SER | CYS | ASP | GLN | PRO | LYS | LEU | LEU | GLY | ILE | GLU | THR | PRO |  |
|  | 50 |  |  |  |  | 55 |  |  |  |  | 60 |  |  |  |  |
| TTG | CCT | AAA | AAG | GAG | TTG | CTC | CTG | CCT | GGG | AAC | AAC | CGG | AAG | GTG | 305 |
| LEU | PRO | LYS | LYS | GLU | LEU | LEU | LEU | PRO | GLY | ASN | ASN | ARG | LYS | VAL |  |
|  | 65 |  |  |  |  | 70 |  |  |  |  | 75 |  |  |  |  |
| TAT | GAA | CTG | AGC | AAT | GTG | CAA | GAA | GAT | AGC | CAA | CCA | ATG | TGC | TAT | 350 |
| TYR | GLU | LEU | SER | ASN | VAL | GLN | GLU | ASP | SER | GLN | PRO | MET | CYS | TYR |  |
|  | 80 |  |  |  |  | 85 |  |  |  |  | 90 |  |  |  |  |
| TCA | AAC | TGC | CCT | GAT | GGG | CAG | TCA | ACA | GCT | AAA | ACC | TTC | CTC | ACC | 395 |
| SER | ASN | CYS | PRO | ASP | GLY | GLN | SER | THR | ALA | LYS | THR | PHE | LEU | THR |  |
|  | 95 |  |  |  |  | 100 |  |  |  |  | 105 |  |  |  |  |
| GTG | TAC | TGG | ACT | CCA | GAA | CGG | GTG | GAA | CTG | GCA | CCC | CTC | CCC | TCT | 440 |
| VAL | TYR | TRP | THR | PRO | GLU | ARG | VAL | GLU | LEU | ALA | PRO | LEU | PRO | SER |  |
|  | 110 |  |  |  |  | 115 |  |  |  |  | 120 |  |  |  |  |
| TGG | CAG | CCA | GTG | GGC | AAG | AAC | CTT | ACC | CTA | CGC | TGC | CAG | GTG | GAG | 485 |
| TRP | GLN | PRO | VAL | GLY | LYS | ASN | LEU | THR | LEU | ARG | CYS | GLN | VAL | GLU |  |
|  | 125 |  |  |  |  | 130 |  |  |  |  | 135 |  |  |  |  |
| GGT | GGG | GCA | CCC | CGG | GCC | AAC | CTC | ACC | GTG | GTG | CTG | CTC | CGT | GGG | 530 |
| GLY | GLY | ALA | PRO | ARG | ALA | ASN | LEU | THR | VAL | VAL | LEU | LEU | ARG | GLY |  |

|     |     |     |     |     |     |     |     |     |     |     |     |     |     |     |      |
|-----|-----|-----|-----|-----|-----|-----|-----|-----|-----|-----|-----|-----|-----|-----|------|
|     | 140 |     |     |     |     | 145 |     |     |     |     |     | 150 |     |     |      |
| GAG | AAG | GAG | CTG | AAA | CGG | GAG | CCA | GCT | GTG | GGG | GAG | CCC | GCT | GAG | 575  |
| GLU | LYS | GLU | LEU | LYS | ARG | GLU | PRO | ALA | VAL | GLY | GLU | PRO | ALA | GLU |      |
|     | 155 |     |     |     |     | 160 |     |     |     |     | 165 |     |     |     |      |
| GTC | ACG | ACC | ACG | GTG | CTG | GTG | AGG | AGA | GAT | CAC | CAT | GGA | GCC | AAT | 620  |
| VAL | THR | THR | THR | VAL | LEU | VAL | ARG | ARG | ASP | HIS | HIS | GLY | ALA | ASN |      |
|     | 170 |     |     |     |     | 175 |     |     |     |     | 180 |     |     |     |      |
| TTC | TCG | TGC | CGC | ACT | GAA | CTG | GAC | CTG | CGG | CCC | CAA | GGG | CTG | GAG | 665  |
| PHE | SER | CYS | ARG | THR | GLU | LEU | ASP | LEU | ARG | PRO | GLN | GLY | LEU | GLU |      |
|     | 185 |     |     |     |     | 190 |     |     |     |     | 195 |     |     |     |      |
| CTG | TTT | GAG | AAC | ACC | TCG | GCC | CCC | TAC | CAG | CTC | CAG | ACC | TTT | GTC | 710  |
| LEU | PHE | GLU | ASN | THR | SER | ALA | PRO | TYR | GLN | LEU | GLN | THR | PHE | VAL |      |
|     | 200 |     |     |     |     | 205 |     |     |     |     | 210 |     |     |     |      |
| CTG | CCA | GCG | ACT | CCC | CCA | CAA | CTT | GTC | AGC | CCC | CGG | GTC | CTA | GAG | 755  |
| LEU | PRO | ALA | THR | PRO | PRO | GLN | LEU | VAL | SER | PRO | ARG | VAL | LEU | GLU |      |
|     | 215 |     |     |     |     | 220 |     |     |     |     | 225 |     |     |     |      |
| GTG | GAC | ACG | CAG | GGG | ACC | GTG | GTC | TGT | TCC | CTG | GAC | GGG | CTG | TTC | 800  |
| VAL | ASP | THR | GLN | GLY | THR | VAL | VAL | CYS | SER | LEU | ASP | GLY | LEU | PHE |      |
|     | 230 |     |     |     |     | 235 |     |     |     |     | 240 |     |     |     |      |
| CCA | GTC | TCG | GAG | GCC | CAG | GTC | CAC | CTG | GCA | CTG | GGG | GAC | CAG | AGG | 845  |
| PRO | VAL | SER | GLU | ALA | GLN | VAL | HIS | LEU | ALA | LEU | GLY | ASP | GLN | ARG |      |
|     | 245 |     |     |     |     | 250 |     |     |     |     | 255 |     |     |     |      |
| TTG | AAC | CCC | ACA | GTC | ACC | TAT | GGC | AAC | GAC | TCC | TTC | TCG | GCC | AAG | 890  |
| LEU | ASN | PRO | THR | VAL | THR | TYR | GLY | ASN | ASP | SER | PHE | SER | ALA | LYS |      |
|     | 260 |     |     |     |     | 265 |     |     |     |     | 270 |     |     |     |      |
| GCC | TCA | GTC | AGT | GTG | ACC | GCA | GAG | GAC | GAG | GGC | ACC | CAG | CGG | CTG | 935  |
| ALA | SER | VAL | SER | VAL | THR | ALA | GLU | ASP | GLU | GLY | THR | GLN | ARG | LEU |      |
|     | 275 |     |     |     |     | 280 |     |     |     |     | 285 |     |     |     |      |
| ACG | TGT | GCA | GTA | ATA | CTG | GGG | AAC | CAG | AGC | CAG | GAG | ACA | CTG | CAG | 980  |
| THR | CYS | ALA | VAL | ILE | LEU | GLY | ASN | GLN | SER | GLN | GLU | THR | LEU | GLN |      |
|     | 290 |     |     |     |     | 295 |     |     |     |     | 300 |     |     |     |      |
| ACA | GTG | ACC | ATC | TAC | AGC | TTT | CCG | GCG | CCC | AAC | GTG | ATT | CTG | ACG | 1025 |
| THR | VAL | THR | ILE | TYR | SER | PHE | PRO | ALA | PRO | ASN | VAL | ILE | LEU | THR |      |
|     | 305 |     |     |     |     | 310 |     |     |     |     | 315 |     |     |     |      |
| AAG | CCA | GAG | GTC | TCA | GAA | GGG | ACC | GAG | GTG | ACA | GTG | AAG | TGT | GAG | 1070 |
| LYS | PRO | GLU | VAL | SER | GLU | GLY | THR | GLU | VAL | THR | VAL | LYS | CYS | GLU |      |
|     | 320 |     |     |     |     | 325 |     |     |     |     | 330 |     |     |     |      |
| GCC | CAC | CCT | AGA | GCC | AAG | GTG | ACG | CTG | AAT | GGG | GTT | CCA | GCC | CAG | 1115 |
| ALA | HIS | PRO | ARG | ALA | LYS | VAL | THR | LEU | ASN | GLY | VAL | PRO | ALA | GLN |      |
|     | 335 |     |     |     |     | 340 |     |     |     |     | 345 |     |     |     |      |
| CCA | CTG | GGC | CCG | AGG | GCC | CAG | CTC | CTG | CTG | AAG | GCC | ACC | CCA | GAG | 1160 |
| PRO | LEU | GLY | PRO | ARG | ALA | GLN | LEU | LEU | LEU | LYS | ALA | THR | PRO | GLU |      |
|     | 350 |     |     |     |     | 355 |     |     |     |     | 360 |     |     |     |      |
| GAC | AAC | GGG | CGC | AGC | TTC | TCC | TGC | TCT | GCA | ACC | CTG | GAG | GTG | GCC | 1205 |
| ASP | ASN | GLY | ARG | SER | PHE | SER | CYS | SER | ALA | THR | LEU | GLU | VAL | ALA |      |
|     | 365 |     |     |     |     | 370 |     |     |     |     | 375 |     |     |     |      |
| GGC | CAG | CTT | ATA | CAC | AAG | AAC | CAG | ACC | CGG | GAG | CTT | CGT | GTC | CTG | 1250 |
| GLY | GLN | LEU | ILE | HIS | LYS | ASN | GLN | THR | ARG | GLU | LEU | ARG | VAL | LEU |      |
|     | 380 |     |     |     |     | 385 |     |     |     |     | 390 |     |     |     |      |
| TAT | GGC | CCC | CGA | CTG | GAC | GAG | AGG | GAT | TGT | CCG | GGA | AAC | TGG | ACG | 1295 |
| TYR | GLY | PRO | ARG | LEU | ASP | GLU | ARG | ASP | CYS | PRO | GLY | ASN | TRP | THR |      |
|     | 395 |     |     |     |     | 400 |     |     |     |     | 405 |     |     |     |      |
| TGG | CCA | GAA | AAT | TCC | CAG | CAG | ACT | CCA | ATG | TGC | CAG | GCT | TGG | GGG | 1340 |
| TRP | PRO | GLU | ASN | SER | GLN | GLN | THR | PRO | MET | CYS | GLN | ALA | TRP | GLY |      |
|     | 410 |     |     |     |     | 415 |     |     |     |     | 420 |     |     |     |      |
| AAC | CCA | TTG | CCC | GAG | CTC | AAG | TGT | CTA | AAG | GAT | GGC | ACT | TTC | CCA | 1385 |
| ASN | PRO | LEU | PRO | GLU | LEU | LYS | CYS | LEU | LYS | ASP | GLY | THR | PHE | PRO |      |
|     | 425 |     |     |     |     | 430 |     |     |     |     | 435 |     |     |     |      |
| CTG | CCC | ATC | GGG | GAA | TCA | GTG | ACT | GTC | ACT | CGA | GAT | CTT | GAG | GGC | 1430 |
| LEU | PRO | ILE | GLY | GLU | SER | VAL | THR | VAL | THR | ARG | ASP | LEU | GLU | GLY |      |

|     |     |     |     |     |     |     |     |     |     |     |     |     |     |      |
|-----|-----|-----|-----|-----|-----|-----|-----|-----|-----|-----|-----|-----|-----|------|
| 440 |     |     |     |     | 445 |     |     |     |     | 450 |     |     |     |      |
| ACC | TAC | CTC | TGT | CGG | GCC | AGG | AGC | ACT | CAA | GGG | GAG | GTC | ACC | CGC | 1475 |
| THR | TYR | LEU | CYS | ARG | ALA | ARG | SER | THR | GLN | GLY | GLU | VAL | THR | ARG |      |
|     | 455 |     |     |     |     | 460 |     |     |     |     | 465 |     |     |     |      |
| GAG | GTG | ACC | GTG | AAT | GTG | CTC | TCC | CCC | CGG | TAT | GAG | ATT | GTC | ATC | 1520 |
| GLU | VAL | THR | VAL | ASN | VAL | LEU | SER | PRO | ARG | TYR | GLU | ILE | VAL | ILE |      |
|     | 470 |     |     |     |     | 475 |     |     |     |     | 480 |     |     |     |      |
| ATC | ACT | GTG | GTA | GCA | GCC | GCA | GTC | ATA | ATG | GGC | ACT | GCA | GGC | CTC | 1565 |
| ILE | THR | VAL | VAL | ALA | ALA | ALA | VAL | ILE | MET | GLY | THR | ALA | GLY | LEU |      |
|     | 485 |     |     |     |     | 490 |     |     |     |     | 495 |     |     |     |      |
| AGC | ACG | TAC | CTC | TAT | AAC | CGC | CAG | CGG | AAG | ATC | AAG | AAA | TAC | AGA | 1610 |
| SER | THR | TYR | LEU | TYR | ASN | ARG | GLN | ARG | LYS | ILE | LYS | LYS | TYR | ARG |      |
|     | 500 |     |     |     |     | 505 |     |     |     |     | 510 |     |     |     |      |
| CTA | CAA | CAG | GCC | CAA | AAA | GGG | ACC | CCC | ATG | AAA | CCG | AAC | ACA | CAA | 1655 |
| LEU | GLN | GLN | ALA | GLN | LYS | GLY | THR | PRO | MET | LYS | PRO | ASN | THR | GLN |      |
|     | 515 |     |     |     |     | 520 |     |     |     |     | 525 |     |     |     |      |
| GCC | ACG | CCT | CCC | TGA |     |     |     |     |     |     |     |     |     |     | 1670 |
| ALA | THR | PRO | PRO | *** |     |     |     |     |     |     |     |     |     |     |      |
|     | 530 |     |     |     |     |     |     |     |     |     |     |     |     |     |      |

| | | | | | |
|---|---|---|---|---|---|
| ACCTATCCCG | GGACAGGGCC | TCTTCCTCGG | CCTTCCCATA | TTGGTGGCAG | 1720 |
| TGGTGCCACA | CTGAACAGAG | TGGAAGACAT | ATGCCATGCA | GCTACACCTA | 1770 |
| CCGGCCCTGG | GACGCCGGAG | GACAGGGCAT | TGTCCTCAGT | CAGATACAAC | 1820 |
| AGCATTTGGG | GCCATGGTAC | CTGCACACCT | AAAACACTAG | GCCACGCATC | 1870 |
| TGATCTGTAG | TCACATGACT | AAGCCAAGAG | GAAGGAGCAA | GACTCAAGAC | 1920 |
| ATGATTGATG | GATGTTAAAG | TCTAGCCTGA | TGAGAGGGA | AGTGGTGGGG | 1970 |
| GAGACATAGC | CCCACCATGA | GGACATACAA | CTGGGAAATA | CTGAAACTTG | 2020 |
| CTGCCTATTG | GGTATGCTGA | GGCCCACAGA | CTTACAGAAG | AAGTGGCCCT | 2070 |
| CCATAGACAT | GTGTAGCATC | AAAACACAAA | GGCCCACACT | TCCTGACGGA | 2120 |
| TGCCAGCTTG | GGCACTGCTG | TCTACTGACC | CCAACCCTTG | ATGATATGTA | 2170 |
| TTTATTCATT | TGTTATTTTA | CCAGCTATTT | ATTGAGTGTC | TTTTATGTAG | 2220 |
| GCTAAATGAA | CATAGGTCTC | TGGCCTCACG | GAGCTCCCAG | TCCATGTCAC | 2270 |
| ATTCAAGGTC | ACCAGGTACA | GTTGTACAGG | TTGTACACTG | CAGGAGAGTG | 2320 |
| CCTGGCAAAA | AGATCAAATG | GGGCTGGGAC | TTCTCATTGG | CCAACCTGCC | 2370 |
| TTTCCCCAGA | AGGAGTGATT | TTTCTATCGG | CACAAAAGCA | CTATATGGAC | 2420 |
| TGGTAATGGT | TCACAGGTTC | AGAGATTACC | CAGTGAGGCC | TTATTCCTCC | 2470 |
| CTTCCCCCCA | AAACTGACAC | CTTTGTTAGC | CACCTCCCCA | CCCACATACA | 2520 |
| TTTCTGCCAG | TGTTACAATG | ACACTCAGCG | GTCATGTCTG | GACATGAGTG | 2570 |
| CCCAGGGAAT | ATGCCCAAGC | TATGCCTTGT | CCTCTTGTCC | TGTTTGCATT | 2620 |
| TCACTGGGAG | CTTGCACTAT | TGCAGCTCCA | GTTTCCTGCA | GTGATCAGGG | 2670 |
| TCCTGCAAGC | AGTGGGGAAG | GGGGCCAAGG | TATTGGAGGA | CTCCCTCCCA | 2720 |
| GCTTTGGAAG | GGTCATCCGC | GTGTGTGTGT | GTGTGTATGT | GTAGACAAGC | 2770 |
| TCTCGCTCTG | TCACCCAGGC | TGGAGTGCAG | TGGTGCAATC | ATGGTTCACT | 2820 |
| GCAGTCTTGA | CCTTTTGGGC | TCAAGTGATC | CTCCCACCTC | AGCCTCCTGA | 2870 |
| GTAGCTGGGA | CCATAGGCTC | ACAACACCAC | ACCTGGCAAA | TTTGATTTTT | 2920 |
| TTTTTTTTTT | TCAGAGACGG | GGTCTCGCAA | CATTGCCCAG | ACTTCCTTTG | 2970 |
| TGTTAGTTAA | TAAAGCTTTC | TCAACTGCCA | AAAAAAAAA | AAAAAA | 3016 |

( 2 ) INFORMATION FOR SEQ ID NO: 98:

( i ) SEQUENCE CHARACTERISTICS:
        ( A ) LENGTH: 3858
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 98:

```
TTCACATCAA  AACTCCTATA  CTGACCTGAG  ACAGAGGCAG  CAGTGATACC                50

CACCTGAGAG  ATCCTGTGTT  TGAACAACTG  CTTCCCAAAA  CGGAAAGTAT               100

TTCAAGCCTA  AACCTTTGGG  TGAAAAGAAC  TCTTGAAGTC  ATG  ATT                 146
                                                 MET  ILE

GCT  TCA  CAG  TTT  CTC  TCA  GCT  CTC  ACT  TTG  GTG  CTT  CTC  ATT  AAA    191
ALA  SER  GLN  PHE  LEU  SER  ALA  LEU  THR  LEU  VAL  LEU  LEU  ILE  LYS
          5                        10                       15

GAG  AGT  GGA  GCC  TGG  TCT  TAC  AAC  ACC  TCC  ACG  GAA  GCT  ATG  ACT    236
GLU  SER  GLY  ALA  TRP  SER  TYR  ASN  THR  SER  THR  GLU  ALA  MET  THR
          20                       25                       30

TAT  GAT  GAG  GCC  AGT  GCT  TAT  TGT  CAG  CAA  AGG  TAC  ACA  CAC  CTG    281
TYR  ASP  GLU  ALA  SER  ALA  TYR  CYS  GLN  GLN  ARG  TYR  THR  HIS  LEU
          35                       40                       45

GTT  GCA  ATT  CAA  AAC  AAA  GAA  GAG  ATT  GAG  TAC  CTA  AAC  TCC  ATA    326
VAL  ALA  ILE  GLN  ASN  LYS  GLU  GLU  ILE  GLU  TYR  LEU  ASN  SER  ILE
          50                       55                       60

TTG  AGC  TAT  TCA  CCA  AGT  TAT  TAC  TGG  ATT  GGA  ATC  AGA  AAA  GTC    371
LEU  SER  TYR  SER  PRO  SER  TYR  TYR  TRP  ILE  GLY  ILE  ARG  LYS  VAL
          65                       70                       75

AAC  AAT  GTG  TGG  GTC  TGG  GTA  GGA  ACC  CAG  AAA  CCT  CTG  ACA  GAA    416
ASN  ASN  VAL  TRP  VAL  TRP  VAL  GLY  THR  GLN  LYS  PRO  LEU  THR  GLU
          80                       85                       90

GAA  GCC  AAG  AAC  TGG  GCT  CCA  GGT  GAA  CCC  AAC  AAT  AGG  CAA  AAA    461
GLU  ALA  LYS  ASN  TRP  ALA  PRO  GLY  GLU  PRO  ASN  ASN  ARG  GLN  LYS
          95                      100                      105

GAT  GAG  GAC  TGC  GTG  GAG  ATC  TAC  ATC  AAG  AGA  GAA  AAA  GAT  GTG    506
ASP  GLU  ASP  CYS  VAL  GLU  ILE  TYR  ILE  LYS  ARG  GLU  LYS  ASP  VAL
          110                     115                      120

GGC  ATG  TGG  AAT  GAT  GAG  AGG  TGC  AGC  AAG  AAG  AAG  CTT  GCC  CTA    551
GLY  MET  TRP  ASN  ASP  GLU  ARG  CYS  SER  LYS  LYS  LYS  LEU  ALA  LEU
          125                     130                      135

TGC  TAC  ACA  GCT  GCC  TGT  ACC  AAT  ACA  TCC  TGC  AGT  GGC  CAC  GGT    596
CYS  TYR  THR  ALA  ALA  CYS  THR  ASN  THR  SER  CYS  SER  GLY  HIS  GLY
          140                     145                      150

GAA  TGT  GTA  GAG  ACC  ATC  AAT  AAT  TAC  ACT  TGC  AAG  TGT  GAC  CCT    641
GLU  CYS  VAL  GLU  THR  ILE  ASN  ASN  TYR  THR  CYS  LYS  CYS  ASP  PRO
          155                     160                      165

GGC  TTC  AGT  GGA  CTC  AAG  TGT  GAG  CAA  ATT  GTG  AAC  TGT  ACA  GCC    686
GLY  PHE  SER  GLY  LEU  LYS  CYS  GLU  GLN  ILE  VAL  ASN  CYS  THR  ALA
          170                     175                      180

CTG  GAA  TCC  CCT  GAG  CAT  GGA  AGC  CTG  GTT  TGC  AGT  CAC  CCA  CTG    731
LEU  GLU  SER  PRO  GLU  HIS  GLY  SER  LEU  VAL  CYS  SER  HIS  PRO  LEU
          185                     190                      195

GGA  AAC  TTC  AGC  TAC  AAT  TCT  TCC  TGC  TCT  ATC  AGC  TGT  GAT  AGG    776
GLY  ASN  PHE  SER  TYR  ASN  SER  SER  CYS  SER  ILE  SER  CYS  ASP  ARG
          200                     205                      210

GGT  TAC  CTG  CCA  AGC  AGC  ATG  GAG  ACC  ATG  CAG  TGT  ATG  TCC  TCT    821
GLY  TYR  LEU  PRO  SER  SER  MET  GLU  THR  MET  GLN  CYS  MET  SER  SER
          215                     220                      225
```

```
GGA  GAA  TGG  AGT  GCT  CCT  ATT  CCA  GCC  TGC  AAT  GTG  GTT  GAG  TGT         866
GLY  GLU  TRP  SER  ALA  PRO  ILE  PRO  ALA  CYS  ASN  VAL  VAL  GLU  CYS
          230                 235                           240

GAT  GCT  GTG  ACA  AAT  CCA  GCC  AAT  GGG  TTC  GTG  GAA  TGT  TTC  CAA         911
ASP  ALA  VAL  THR  ASN  PRO  ALA  ASN  GLY  PHE  VAL  GLU  CYS  PHE  GLN
          245                 250                           255

AAC  CCT  GGA  AGC  TTC  CCA  TGG  AAC  ACA  ACC  TGT  ACA  TTT  GAC  TGT         956
ASN  PRO  GLY  SER  PHE  PRO  TRP  ASN  THR  THR  CYS  THR  PHE  ASP  CYS
          260                 265                           270

GAA  GAA  GGA  TTT  GAA  CTA  ATG  GGA  GCC  CAG  AGC  CTT  CAG  TGT  ACC        1001
GLU  GLU  GLY  PHE  GLU  LEU  MET  GLY  ALA  GLN  SER  LEU  GLN  CYS  THR
          275                 280                           285

TCA  TCT  GGG  AAT  TGG  GAC  AAC  GAG  AAG  CCA  ACG  TGT  AAA  GCT  GTG        1046
SER  SER  GLY  ASN  TRP  ASP  ASN  GLU  LYS  PRO  THR  CYS  LYS  ALA  VAL
          290                 295                           300

ACA  TGC  AGG  GCC  GTC  CGC  CAG  CCT  CAG  AAT  GGC  TCT  GTG  AGG  TGC        1091
THR  CYS  ARG  ALA  VAL  ARG  GLN  PRO  GLN  ASN  GLY  SER  VAL  ARG  CYS
          305                 310                           315

AGC  CAT  TCC  CCT  GCT  GGA  GAG  TTC  ACC  TTC  AAA  TCA  TCC  TGC  AAC        1136
SER  HIS  SER  PRO  ALA  GLY  GLU  PHE  THR  PHE  LYS  SER  SER  CYS  ASN
          320                 325                           330

TTC  ACC  TGT  GAG  GAA  GGC  TTC  ATG  TTG  CAG  GGA  CCA  GCC  CAG  GTT        1181
PHE  THR  CYS  GLU  GLU  GLY  PHE  MET  LEU  GLN  GLY  PRO  ALA  GLN  VAL
          335                 360                           370

GAA  TGC  ACC  ACT  CAA  GGG  CAG  TGG  ACA  CAG  CAA  ATC  CCA  GTT  TGT        1226
GLU  CYS  THR  THR  GLN  GLY  GLN  TRP  THR  GLN  GLN  ILE  PRO  VAL  CYS
          375                 380                           385

GAA  GCT  TTC  CAG  TGC  ACA  GCC  TTG  TCC  AAC  CCC  GAG  CGA  GGC  TAC        1271
GLU  ALA  PHE  GLN  CYS  THR  ALA  LEU  SER  ASN  PRO  GLU  ARG  GLY  TYR
          390                 395                           400

ATG  AAT  TGT  CTT  CCT  AGT  GCT  TCT  GGC  AGT  TTC  CGT  TAT  GGG  TCC        1316
MET  ASN  CYS  LEU  PRO  SER  ALA  SER  GLY  SER  PHE  ARG  TYR  GLY  SER
          405                 410                           415

AGC  TGT  GAG  TTC  TCC  TGT  GAG  CAG  GGT  TTT  GTG  TTG  AAG  GGA  TCC        1361
SER  CYS  GLU  PHE  SER  CYS  GLU  GLN  GLY  PHE  VAL  LEU  LYS  GLY  SER
          420                 425                           430

AAA  AGG  CTC  CAA  TGT  GGC  CCC  ACA  GGG  GAG  TGG  GAC  AAC  GAG  AAG        1406
LYS  ARG  LEU  GLN  CYS  GLY  PRO  THR  GLY  GLU  TRP  ASP  ASN  GLU  LYS
          435                 440                           445

CCC  ACA  TGT  GAA  GCT  GTG  AGA  TGC  GAT  GCT  GTC  CAC  CAG  CCC  CCG        1451
PRO  THR  CYS  GLU  ALA  VAL  ARG  CYS  ASP  ALA  VAL  HIS  GLN  PRO  PRO
          450                 455                           460

AAG  GGT  TTG  GTG  AGG  TGT  GCT  CAT  TCC  CCT  ATT  GGA  GAA  TTC  ACC        1496
LYS  GLY  LEU  VAL  ARG  CYS  ALA  HIS  SER  PRO  ILE  GLY  GLU  PHE  THR
          465                 470                           475

TAC  AAG  TCC  TCT  TGT  GCC  TTC  AGC  TGT  GAG  GAG  GGA  TTT  GAA  TTA        1541
TYR  LYS  SER  SER  CYS  ALA  PHE  SER  CYS  GLU  GLU  GLY  PHE  GLU  LEU
          480                 485                           490

TAT  GGA  TCA  ACT  CAA  CTT  GAG  TGC  ACA  TCT  CAG  GGA  CAA  TGG  ACA        1586
TYR  GLY  SER  THR  GLN  LEU  GLU  CYS  THR  SER  GLN  GLY  GLN  TRP  THR
          495                 500                           505

GAA  GAG  GTT  CCT  TCC  TGC  CAA  GTG  GTA  AAA  TGT  TCA  AGC  CTG  GCA        1631
GLU  GLU  VAL  PRO  SER  CYS  GLN  VAL  VAL  LYS  CYS  SER  SER  LEU  ALA
          510                 515                           520

GTT  CCG  GGA  AAG  ATC  AAC  ATG  AGC  TGC  AGT  GGG  GAG  CCC  GTG  TTT        1676
VAL  PRO  GLY  LYS  ILE  ASN  MET  SER  CYS  SER  GLY  GLU  PRO  VAL  PHE
          525                 530                           535

GGC  ACT  GTG  TGC  AAG  TTC  GCC  TGT  CCT  GAA  GGA  TGG  ACG  CTC  AAT        1721
GLY  THR  VAL  CYS  LYS  PHE  ALA  CYS  PRO  GLU  GLY  TRP  THR  LEU  ASN
          540                 545                           550
```

| | | | | | | | | | | | | | | | |
|---|---|---|---|---|---|---|---|---|---|---|---|---|---|---|---|
| GGC | TCT | GCA | GCT | CGG | ACA | TGT | GGA | GCC | ACA | GGA | CAC | TGG | TCT | GGC | 1766 |
| GLY | SER | ALA | ALA | ARG | THR | CYS | GLY | ALA | THR | GLY | HIS | TRP | SER | GLY | |
| | | 555 | | | | 560 | | | | | 565 | | | | |
| CTG | CTA | CCT | ACC | TGT | GAA | GCT | CCC | ACT | GAG | TCC | AAC | ATT | CCC | TTG | 1811 |
| LEU | LEU | PRO | THR | CYS | GLU | ALA | PRO | THR | GLU | SER | ASN | ILE | PRO | LEU | |
| | | 570 | | | | 575 | | | | | 580 | | | | |
| GTA | GCT | GGA | CTT | TCT | GCT | GCT | GGA | CTC | TCC | CTC | CTG | ACA | TTA | GCA | 1856 |
| VAL | ALA | GLY | LEU | SER | ALA | ALA | GLY | LEU | SER | LEU | LEU | THR | LEU | ALA | |
| | | 585 | | | | 590 | | | | | 595 | | | | |
| CCA | TTT | CTC | CTC | TGG | CTT | CGG | AAA | TGC | TTA | CGG | AAA | GCA | AAG | AAA | 1901 |
| PRO | PHE | LEU | LEU | TRP | LEU | ARG | LYS | CYS | LEU | ARG | LYS | ALA | LYS | LYS | |
| | | 600 | | | | 605 | | | | | 610 | | | | |
| TTT | GTT | CCT | GCC | AGC | AGC | TGC | CAA | AGC | CTT | GAA | TCA | GAC | GGA | AGC | 1946 |
| PHE | VAL | PRO | ALA | SER | SER | CYS | GLN | SER | LEU | GLU | SER | ASP | GLY | SER | |
| | | 615 | | | | 620 | | | | | 625 | | | | |
| TAC | CAA | AAG | CCT | TCT | TAC | ATC | CTT | TAA | GTTCAAA | AGAATCAGAA | | | | | 1990 |
| TYR | GLN | LYS | PRO | SER | TYR | ILE | LEU | *** | | | | | | | |
| | | 630 | | | | 635 | | | | | | | | | |

| | | | | |
|---|---|---|---|---|
| ACAGGTGCAT | CTGGGGAACT | AGAGGGATAC | ACTGAAGTTA | ACAGAGACAG | 2040 |
| ATAACTCTCC | TCGGGTCTCT | GGCCCTTCTT | GCCTACTATG | CCAGATGCCT | 2090 |
| TTATGGCTGA | AACCGCAACA | CCCATCACCA | CTTCAATAGA | TCAAAGTCCA | 2140 |
| GCAGGCAAGG | ACGGCCTTCA | ACTGAAAAGA | CTCAGTGTTC | CCTTTCCTAC | 2190 |
| TCTCAGGATC | AAGAAAGTGT | TGGCTAATGA | AGGGAAAGGA | TATTTTCTTC | 2240 |
| CAAGCAAAGG | TGAAGAGACC | AAGACTCTGA | AATCTCAGAA | TTCCTTTTCT | 2290 |
| AACTCTCCCT | TGCTCGCTGT | AAAATCTTGG | CACAGAAACA | CAATATTTTG | 2340 |
| TGGCTTTCTT | TCTTTTGCCC | TTCACAGTGT | TTCGACAGCT | GATTACACAG | 2390 |
| TTGCTGTCAT | AAGAATGAAT | AATAATTATC | CAGAGTTTAG | AGGAAAAAAA | 2440 |
| TGACTAAAAA | TATTATAACT | TAAAAAAATG | ACAGATGTTG | AATGCCCACA | 2490 |
| GGCAAATGCA | TGGAGGGTTG | TTAATGGTGC | AAATCCTACT | GAATGCTCTG | 2540 |
| TGCGAGGGTT | ACTATGCACA | ATTTAATCAC | TTTCATCCCT | ATGGGATTCA | 2590 |
| GTGCTTCTTA | AAGAGTTCTT | AAGGATTGTG | ATATTTTTAC | TTGCATTGAA | 2640 |
| TATATTATAA | TCTTCCATAC | TTCTTCATTC | AATACAAGTG | TGGTAGGGAC | 2690 |
| TTAAAAAACT | TGTAAATGCT | GTCAACTATG | ATATGGTAAA | AGTTACTTAT | 2740 |
| TCTAGATTAC | CCCCTCATTG | TTTATTAACA | AATTATGTTA | CATCTGTTTT | 2790 |
| AAATTTATTT | CAAAAAGGGA | AACTATTGTC | CCCTAGCAAG | GCATGATGTT | 2840 |
| AACCAGAATA | AAGTTCTGAG | TGTTTTTACT | ACAGTTGTTT | TTTGAAAACA | 2890 |
| TGGTAGAATT | GGAGAGTAAA | AACTGAATGG | AAGGTTTGTA | TATTGTCAGA | 2940 |
| TATTTTTTCA | GAAATATGTG | GTTTCCACGA | TGAAAAACTT | CCATGAGGCC | 2990 |
| AAACGTTTTG | AACTAATAAA | AGCATAAATG | CAAACACACA | AAGGTATAAT | 3040 |
| TTTATGAATG | TCTTTGTTGG | AAAAGAATAC | AGAAGATGG | ATGTGCTTTG | 3090 |
| CATTCCTACA | AAGATGTTTG | TCAGATGTGA | TATGTAAACA | TAATTCTTGT | 3140 |
| ATATTATGGA | AGATTTTAAA | TTCACAATAG | AAACTCACCA | TGTAAAAGAG | 3190 |
| TCATCTGGTA | GATTTTTAAC | GAATGAAGAT | GTCTAATAGT | TATTCCCTAT | 3240 |
| TTGTTTTCTT | CTGTATGTTA | GGGTGCTCTG | GAAGAGAGGA | ATGCCTGTGT | 3290 |
| GAGCAAGCAT | TTATGTTTAT | TTATAAGCAG | ATTTAACAAT | TCCAAAGGAA | 3340 |
| TCTCCAGTTT | TCAGTTGATC | ACTGGCAATG | AAAAATTCTC | AGTCAGTAAT | 3390 |

| | |
|---|---|
| TGCCAAAGCT GCTCTAGCCT TGAGGAGTGT GAGAATCAAA ACTCTCCTAC | 3440 |
| ACTTCCATTA ACTTAGCATG TGTTGAAAAA AAAAGTTTCA GAGAAGTTCT | 3490 |
| GGCTGAACAC TGGCAACGAC AAAGCCAACA GTCAAAACAG AGATGTGATA | 3540 |
| AGGATCAGAA CAGCAGAGGT TCTTTTAAAG GGGCAGAAAA ACTCTGGGAA | 3590 |
| ATAAGAGAGA ACAACTACTG TGATCAGGCT ATGTATGGAA TACAGTGTTA | 3640 |
| TTTTCTTTGA AATTGTTTAA GTGTTGTAAA TATTTATGTA AACTGCATTA | 3690 |
| GAAATTAGCT GTGTGAAATA CCAGTGTGG TTGTGTTTGA GTTTTATTGA | 3740 |
| GAATTTTAAA TTATAACTTA AAATATTTTA TAATTTTTAA AGTATATATT | 3790 |
| TATTTAAGCT TATGTCAGAC CTATTTGACA TAACACTATA AAGGTTGACA | 3840 |
| ATAAATGTGC TTATGTTT | 3858 |

(2) INFORMATION FOR SEQ ID NO: 99:

(i) SEQUENCE CHARACTERISTICS:
        (A) LENGTH: 2813
        (B) TYPE: NUCLEIC ACID
        (C) STRANDEDNESS: SINGLE
        (D) TOPOLOGY: LINEAR (iv) ANTI-SENSE: No (xi) SEQUENCE DESCRIPTION: SEQ ID NO: 99:

| | |
|---|---|
| CGGGCCTCAC TGGCTTCAGG AGCTGAATAC CCTCCCAGGC ACACACAGGT | 50 |
| GGGACACAAA TAAGGGTTTT GGAACCACTA TTTTCTCATC ACGACAGCAA | 100 |

| | |
|---|---|
| CTTAAA ATG CCT GGG AAG ATG GTC GTG ATC CTT GGA GCC | 139 |
|       MET PRO GLY LYS MET VAL VAL ILE LEU GLY ALA | |
|                    5                   10 | |
| TCA AAT ATA CTT TGG ATA ATG TTT GCA GCT TCT CAA GCT TTT AAA | 184 |
| SER ASN ILE LEU TRP ILE MET PHE ALA ALA SER GLN ALA PHE LYS | |
|          15                  20               25 | |
| ATC GAG ACC ACC CCA GAA TCT AGA TAT CTT GCT CAG ATT GGT GAC | 229 |
| ILE GLU THR THR PRO GLU SER ARG TYR LEU ALA GLN ILE GLY ASP | |
|          30                  35               40 | |
| TCC GTC TCA TTG ACT TGC AGC ACC ACA GGC TGT GAG TCC CCA TTT | 274 |
| SER VAL SER LEU THR CYS SER THR THR GLY CYS GLU SER PRO PHE | |
|          45                  50               55 | |
| TTC TCT TGG AGA ACC CAG ATA GAT AGT CCA CTG AAT GGG AAG GTG | 319 |
| PHE SER TRP ARG THR GLN ILE ASP SER PRO LEU ASN GLY LYS VAL | |
|          60                  65               70 | |
| ACG AAT GAG GGG ACC ACA TCT ACG CTG ACA ATG AAT CCT GTT AGT | 364 |
| THR ASN GLU GLY THR THR SER THR LEU THR MET ASN PRO VAL SER | |
|          75                  80               85 | |
| TTT GGG AAC GAA CAC TCT TAC CTG TGC ACA GCA ACT TGT GAA TCT | 409 |
| PHE GLY ASN GLU HIS SER TYR LEU CYS THR ALA THR CYS GLU SER | |
|          90                  95             100 | |
| AGG AAA TTG GAA AAA GGA ATC CAG GTG GAG ATC TAC TCT TTT CCT | 454 |
| ARG LYS LEU GLU LYS GLY ILE GLN VAL GLU ILE TYR SER PHE PRO | |
|         105                 110            115 | |
| AAG GAT CCA GAG ATT CAT TTG AGT GGC CCT CTG GAG GCT GGG AAG | 499 |
| LYS ASP PRO GLU ILE HIS LEU SER GLY PRO LEU GLU ALA GLY LYS | |
|         120                 125            130 | |
| CCG ATC ACA GTC AAG TGT TCA GTT GCT GAT GTA TAC CCA TTT GAC | 544 |
| PRO ILE THR VAL LYS CYS SER VAL ALA ASP VAL TYR PRO PHE ASP | |
|         135                 140            145 | |
| AGG CTG GAG ATA GAC TTA CTG AAA GGA GAT CAT CTC ATG AAG AGT | 589 |
| ARG LEU GLU ILE ASP LEU LEU LYS GLY ASP HIS LEU MET LYS SER | |
|         150                 155            160 | |

| | | | | | | | | | | | | | | | |
|---|---|---|---|---|---|---|---|---|---|---|---|---|---|---|---|
| CAG | GAA | TTT | CTG | GAG | GAT | GCA | GAC | AGG | AAG | TCC | CTG | GAA | ACC | AAG | 634 |
| GLN | GLU | PHE | LEU | GLU | ASP | ALA | ASP | ARG | LYS | SER | LEU | GLU | THR | LYS | |
| | | 165 | | | | | 170 | | | | | 175 | | | |
| AGT | TTG | GAA | GTA | ACC | TTT | ACT | CCT | GTC | ATT | GAG | GAT | ATT | GGA | AAA | 679 |
| SER | LEU | GLU | VAL | THR | PHE | THR | PRO | VAL | ILE | GLU | ASP | ILE | GLY | LYS | |
| | | 180 | | | | | 185 | | | | | 190 | | | |
| GTT | CTT | GTT | TGC | CGA | GCT | AAA | TTA | CAC | ATT | GAT | GAA | ATG | GAT | TCT | 724 |
| VAL | LEU | VAL | CYS | ARG | ALA | LYS | LEU | HIS | ILE | ASP | GLU | MET | ASP | SER | |
| | | 195 | | | | | 200 | | | | | 205 | | | |
| GTG | CCC | ACA | GTA | AGG | CAG | GCT | GTA | AAA | GAA | TTG | CAA | GTC | TAC | ATA | 769 |
| VAL | PRO | THR | VAL | ARG | GLN | ALA | VAL | LYS | GLU | LEU | GLN | VAL | TYR | ILE | |
| | | 210 | | | | | 215 | | | | | 220 | | | |
| TCA | CCC | AAG | AAT | ACA | GTT | ATT | TCT | GTG | AAT | CCA | TCC | ACA | AAG | CTG | 814 |
| SER | PRO | LYS | ASN | THR | VAL | ILE | SER | VAL | ASN | PRO | SER | THR | LYS | LEU | |
| | | 225 | | | | | 230 | | | | | 235 | | | |
| CAA | GAA | GGT | GGC | TCT | GTG | ACC | ATG | ACC | TGT | TCC | AGC | GAG | GGT | CTA | 859 |
| GLN | GLU | GLY | GLY | SER | VAL | THR | MET | THR | CYS | SER | SER | GLU | GLY | LEU | |
| | | 240 | | | | | 245 | | | | | 250 | | | |
| CCA | GCT | CCA | GAG | ATT | TTC | TGG | AGT | AAG | AAA | TTA | GAT | AAT | GGG | AAT | 904 |
| PRO | ALA | PRO | GLU | ILE | PHE | TRP | SER | LYS | LYS | LEU | ASP | ASN | GLY | ASN | |
| | | 255 | | | | | 260 | | | | | 265 | | | |
| CTA | CAG | CAC | CTT | TCT | GGA | AAT | GCA | ACT | CTC | ACC | TTA | ATT | GCT | ATG | 949 |
| LEU | GLN | HIS | LEU | SER | GLY | ASN | ALA | THR | LEU | THR | LEU | ILE | ALA | MET | |
| | | 270 | | | | | 275 | | | | | 280 | | | |
| AGG | ATG | GAA | GAT | TCT | GGA | ATT | TAT | GTG | TGT | GAA | GGA | GTT | AAT | TTG | 994 |
| ARG | MET | GLU | ASP | SER | GLY | ILE | TYR | VAL | CYS | GLU | GLY | VAL | ASN | LEU | |
| | | 285 | | | | | 290 | | | | | 295 | | | |
| ATT | GGG | AAA | AAC | AGA | AAA | GAG | GTG | GAA | TTA | ATT | GTT | CAA | GCA | TTC | 1039 |
| ILE | GLY | LYS | ASN | ARG | LYS | GLU | VAL | GLU | LEU | ILE | VAL | GLN | ALA | PHE | |
| | | 300 | | | | | 305 | | | | | 310 | | | |
| CCT | AGA | GAT | CCA | GAA | ATC | GAG | ATG | AGT | GGT | GGC | CTC | GTG | AAT | GGG | 1084 |
| PRO | ARG | ASP | PRO | GLU | ILE | GLU | MET | SER | GLY | GLY | LEU | VAL | ASN | GLY | |
| | | 315 | | | | | 320 | | | | | 325 | | | |
| AGC | TCT | GTC | ACT | GTA | AGC | TGC | AAG | GTT | CCT | AGC | GTG | TAC | CCC | CTT | 1129 |
| SER | SER | VAL | THR | VAL | SER | CYS | LYS | VAL | PRO | SER | VAL | TYR | PRO | LEU | |
| | | 330 | | | | | 335 | | | | | 340 | | | |
| GAC | CGG | CTG | GAG | ATT | GAA | TTA | CTT | AAG | GGG | GAG | ACT | ATT | CTG | GAG | 1174 |
| ASP | ARG | LEU | GLU | ILE | GLU | LEU | LEU | LYS | GLY | GLU | THR | ILE | LEU | GLU | |
| | | 345 | | | | | 350 | | | | | 355 | | | |
| AAT | ATA | GAG | TTT | TTG | GAG | GAT | ACG | GAT | ATG | AAA | TCT | CTA | GAG | AAC | 1219 |
| ASN | ILE | GLU | PHE | LEU | GLU | ASP | THR | ASP | MET | LYS | SER | LEU | GLU | ASN | |
| | | 360 | | | | | 365 | | | | | 370 | | | |
| AAA | AGT | TTG | GAA | ATG | ACC | TTC | ATC | CCT | ACC | ATT | GAA | GAT | ACT | GGA | 1264 |
| LYS | SER | LEU | GLU | MET | THR | PHE | ILE | PRO | THR | ILE | GLU | ASP | THR | GLY | |
| | | 375 | | | | | 380 | | | | | 385 | | | |
| AAA | GCT | CTT | GTT | TGT | CAG | GCT | AAG | TTA | CAT | ATT | GAT | GAC | ATG | GAA | 1309 |
| LYS | ALA | LEU | VAL | CYS | GLN | ALA | LYS | LEU | HIS | ILE | ASP | ASP | MET | GLU | |
| | | 390 | | | | | 395 | | | | | 400 | | | |
| TTC | GAA | CCC | AAA | CAA | AGG | CAG | AGT | ACG | CAA | ACA | CTT | TAT | GTC | AAT | 1354 |
| PHE | GLU | PRO | LYS | GLN | ARG | GLN | SER | THR | GLN | THR | LEU | TYR | VAL | ASN | |
| | | 405 | | | | | 410 | | | | | 415 | | | |
| GTT | GCC | CCC | AGA | GAT | ACA | ACC | GTC | TTG | GTC | AGC | CCT | TCC | TCC | ATC | 1399 |
| VAL | ALA | PRO | ARG | ASP | THR | THR | VAL | LEU | VAL | SER | PRO | SER | SER | ILE | |
| | | 420 | | | | | 425 | | | | | 430 | | | |
| CTG | GAG | GAA | GGC | AGT | TCT | GTG | AAT | ATG | ACA | TGC | TTG | AGC | CAG | GGC | 1444 |
| LEU | GLU | GLU | GLY | SER | SER | VAL | ASN | MET | THR | CYS | LEU | SER | GLN | GLY | |
| | | 435 | | | | | 440 | | | | | 445 | | | |
| TTT | CCT | GCT | CCG | AAA | ATC | CTG | TGG | AGC | AGG | CAG | CTC | CCT | AAC | GGG | 1489 |
| PHE | PRO | ALA | PRO | LYS | ILE | LEU | TRP | SER | ARG | GLN | LEU | PRO | ASN | GLY | |
| | | 450 | | | | | 455 | | | | | 460 | | | |

| | | |
|---|---|---|
| GAG CTA CAG CCT CTT TCT GAG AAT GCA ACT CTC ACC TTA ATT TCT<br>GLU LEU GLN PRO LEU SER GLU ASN ALA THR LEU THR LEU ILE SER<br>465 470 475 | | 1534 |
| ACA AAA ATG GAA GAT TCT GGG GTT TAT TTA TGT GAA GGA ATT AAC<br>THR LYS MET GLU ASP SER GLY VAL TYR LEU CYS GLU GLY ILE ASN<br>480 485 490 | | 1579 |
| CAG GCT GGA AGA AGC AGA AAG GAA GTG GAA TTA ATT ATC CAA GTT<br>GLN ALA GLY ARG SER ARG LYS GLU VAL GLU LEU ILE ILE GLN VAL<br>495 500 505 | | 1624 |
| ACT CCA AAA GAC ATA AAA CTT ACA GCT TTT CCT TCT GAG AGT GTC<br>THR PRO LYS ASP ILE LYS LEU THR ALA PHE PRO SER GLU SER VAL<br>510 515 520 | | 1669 |
| AAA GAA GGA GAC ACT GTC ATC ATC TCT TGT ACA TGT GGA AAT GTT<br>LYS GLU GLY ASP THR VAL ILE ILE SER CYS THR CYS GLY ASN VAL<br>525 530 535 | | 1714 |
| CCA GAA ACA TGG ATA ATC CTG AAG AAA AAA GCG GAG ACA GGA GAC<br>PRO GLU THR TRP ILE ILE LEU LYS LYS LYS ALA GLU THR GLY ASP<br>540 545 550 | | 1759 |
| ACA GTA CTA AAA TCT ATA GAT GGC GCC TAT ACC ATC CGA AAG GCC<br>THR VAL LEU LYS SER ILE ASP GLY ALA TYR THR ILE ARG LYS ALA<br>555 560 565 | | 1804 |
| CAG TTG AAG GAT GCG GGA GTA TAT GAA TGT GAA TCT AAA AAC AAA<br>GLN LEU LYS ASP ALA GLY VAL TYR GLU CYS GLU SER LYS ASN LYS<br>570 575 580 | | 1849 |
| GTT GGC TCA CAA TTA AGA AGT TTA ACA CTT GAT GTT CAA GGA AGA<br>VAL GLY SER GLN LEU ARG SER LEU THR LEU ASP VAL GLN GLY ARG<br>585 590 595 | | 1894 |
| GAA AAC AAC AAA GAC TAT TTT TCT CCT GAG CTT CTC GTG CTC TAT<br>GLU ASN ASN LYS ASP TYR PHE SER PRO GLU LEU LEU VAL LEU TYR<br>600 605 610 | | 1939 |
| TTT GCA TCC TCC TTA ATA ATA CCT GCC ATT GGA ATG ATA ATT TAC<br>PHE ALA SER SER LEU ILE ILE PRO ALA ILE GLY MET ILE ILE TYR<br>615 620 625 | | 1984 |
| TTT GCA AGA AAA GCC AAC ATG AAG GGG TCA TAT AGT CTT GTA GAA<br>PHE ALA ARG LYS ALA ASN MET LYS GLY SER TYR SER LEU VAL GLU<br>630 635 640 | | 2029 |
| GCA CAG AAA TCA AAA GTG TAG<br>ALA GLN LYS SER LYS VAL ***<br>645 | | 2050 |
| CTAATGCTTG ATATGTTCAA CTGGAGACAC TATTTATCTG TGCAAATCCT | | 2100 |
| TGATACTGCT CATCATTCCT TGAGAAAAAC AATGAGCTGA GAGGCAGACT | | 2150 |
| TCCCTGAATG TATTGAACTT GGAAAGAAAT GCCCATCTAT GTCCCTTGCT | | 2200 |
| GTGAGCAAGA AGTCAAAGTA AAACTTGCTG CCTGAAGAAC AGTAACTGCC | | 2250 |
| ATCAAGATGA GAGAACTGGA GGAGTTCCTT GATCTGTATA TACAATAACA | | 2300 |
| TAATTTGTAC ATATGTAAAA TAAAATTATG CCATAGCAAG ATTGCTTAAA | | 2350 |
| ATAGCAACAC TCTATATTTA GATTGTTAAA ATAACTAGTG TTGCTTGGAC | | 2400 |
| TATTATAATT TAATGCATGT TAGGAAAATT TCACATTAAT ATTTGCTGAC | | 2450 |
| AGCTGACCTT TGTCATCTTT CTTCTATTTT ATTCCCTTTC ACAAAATTTT | | 2500 |
| ATTCCTATAT AGTTTATTGA CAATAATTTC AGGTTTTGTA AAGATGCCGG | | 2550 |
| GTTTTATATT TTTATAGACA ATAATAAGC AAAGGGAGCA CTGGGTTGAC | | 2600 |
| TTTCAGGTAC TAAATACCTC AACCTATGGT ATAATGGTTG ACTGGGTTTC | | 2650 |
| TCTGTATAGT ACTGGCATGG TACGGAGATG TTTCACGAAG TTTGTTCATC | | 2700 |
| AGACTCCTGT GCAACTTTCC CAATGTGGCC TAAAAATGCA ACTTCTTTTT | | 2750 |

```
ATTTTCTTTT    GTAAATGTTT    AGGTTTTTTT    GTATAGTAAA    GTGATAATTT                    2800

CTGGAATTAA    AAA                                                                     2813
```